(12) United States Patent
Shimura et al.

(10) Patent No.: US 6,654,695 B2
(45) Date of Patent: Nov. 25, 2003

(54) DEMENTIA TEST APPARATUS, DEMENTIA TEST SERVER, DEMENTIA TEST CLIENT AND DEMENTIA TEST SYSTEM

(75) Inventors: Takaki Shimura, Hiratsuka (JP); Mitsuo Kaneko, Hamamatsu (JP); Sohta Shimizu, Hiratsuka (JP); Yuichi Iguchi, Hiratsuka (JP)

(73) Assignee: Tokai University Educational System, Tokyo (JP)

( * ) Notice: Subject to any disclaimer, the term of this patent is extended or adjusted under 35 U.S.C. 154(b) by 79 days.

(21) Appl. No.: 09/987,055

(22) Filed: Nov. 13, 2001

(65) Prior Publication Data
US 2002/0059031 A1 May 16, 2002

(30) Foreign Application Priority Data
Nov. 13, 2000 (JP) ........................ 2000-345315

(51) Int. Cl.⁷ .............................................. G09B 3/12
(52) U.S. Cl. ........................................ 702/19; 434/350
(58) Field of Search ................................. 702/19, 81, 82, 702/84, 179, 180, 181, 182, 183, 187, 32, 108; 600/544, 300; 706/20, 47; 700/104, 108, 300; 434/236, 238, 327, 350

(56) References Cited
U.S. PATENT DOCUMENTS

| | | | | |
|---|---|---|---|---|
| 4,770,636 A | * | 9/1988 | Buschke | 434/236 |
| 4,895,518 A | * | 1/1990 | Arnold et al. | 434/118 |
| 5,226,819 A | * | 7/1993 | Takagaki | 434/236 |
| 6,053,866 A | * | 4/2000 | McLeod | 600/300 |
| 6,565,359 B2 | * | 5/2003 | Calhoun et al. | 434/236 |

* cited by examiner

Primary Examiner—Marc S. Hoff
Assistant Examiner—Edward Raymond
(74) Attorney, Agent, or Firm—Sughrue Mion, PLLC

(57) ABSTRACT

The present invention relates to a dementia test system and the like for testing a dementia degree of a testee, and provides a dementia test system which is effective for preventing and finding, at early stage, an initial sign (initial dementia) of senile dementia. A dementia test apparatus comprising an answer obtaining section 131 for obtaining an answer of a testee to both a dementia degree test chart which requires a plurality kinds of judgment at the same time and obtains an answer in such a form that correction of judgement is objectively judged, and a dementia factor degree test chart comprising a combination of a plurality of question concerning sensibility and a plurality of answers alternatively selected from questions prepared for each of the former questions, and a dementia degree test section 132 for testing a dementia degree indicative of a current degree of dementia of the testee based on an answer obtained by the answer obtaining section, and for estimating transition of future dementia degree of the testee.

26 Claims, 23 Drawing Sheets

| RED | VIOLET | YELLOW | BLUE | BLACK |
|---|---|---|---|---|
| VIOLET | BLACK | GREEN | YELLOW | VIOLET |
| BLUE | RED | YELLOW | VIOLET | BLACK |
| BLACK | GREEN | RED | YELLOW | BLUE |
| BLACK | RED | VIOLET | BLUE | YELLOW |
| BLUE | YELLOW | GREEN | RED | BLACK |
| RED | GREEN | YELLOW | VIOLET | RED |
| YELLOW | BLACK | BLUE | VIOLET | GREEN |

Fig. 4

CHARACTER PICK-UP TEST

Select and put ○ on "a, b, c, d, e" while understanding the meaning of the following characters .

(Time limit is two minutes.)

Once upon a time, an old lady in single was living somewhere. She was old and poor, but always bright. She was living in a small lodge, helped neighbors and received foods, lived single from hand to mouth, but it seemed that she was always fine, bright and had no grievances. However, one night, when she brightly returned to her home as usual, she found a black big pot. She said "There is a pot, this is convenient if I have something to be put in the pot, but I do not. I wonder who dropped the pot". She looked around to check if there is some one, but found no one. She said "The pot had a hole in it and was discarded, I will take the pot", and she picked up a lid of the pot and took a look inside.

Fig. 5

< SCORE OF THE CHARACTER PICK-UP TEST >

1. Search of vowels

\* correct ( ), \* incorrect ( ), \* oversight ( )

2. Understanding of contents (answer the following questions (1) to (10) with ○ and ×)

(1) The old lady was living with an old man.

(2) The old lady was always fine and bright.

(3) The old lady was rich and living in a palace.

(4) The old lady helped neighbors.

(5) The old lady found a pot on the road.

(6) The pot was small.

(7) The pot was black.

(8) The old lady left the pot.

(9) The pot was closed with a lid.

(10) There were two pots.

Fig. 6

1. Married man 1.1 Daily life

| | Question | Group1 | Group2 | Group3 |
|---|---|---|---|---|
| 1 | Can you have a joke with your wife of family? | I can make naturally. | I intentionally make. | I seldom make. |
| 2 | Do you compliment your wife? | I can compliment naturally. | I sometimes compliment | I seldom compliment |
| 3 | Do you select your cloth with your wife? | I always select with my wife. | I usually select by myself. | I leave it to my wife. |
| 4 | Do you consult with your wife about house work, parenting, contact with cousinry? | I can brightly consult with my wife. | I feel troublesome but I do. | I take things as granted, for example, "○○ is ××". |
| 5 | Do you like music and painting? | I sometimes appreciate with my wife. | I sometimes talk with my wife about them. | I am not interested. |
| 6 | Do you go Karaoke? | I sometimes go with my wife or family. | I have been to Karaoke with my wife or family for a few times. | I do not like singing. |
| 7 | Do you enjoy holiday with your family? | I go driving or travel with my family because I am unloaded. | I do not like, but I go with my family for service. | I take a rest at in home and this is the best. |
| 8 | Do you play Igo, Shougi, Hanafuda, play cards or majan? | I have confidence. | I do but for service. | I do not like game or bet. |
| 9 | Do you play musical instrument, draw painting, enjoy sports such as baseball, golf, ski? | I have something that I can be enthusiastic. | If I have time, I want to do something. | I am not interested in hobby or sports. |
| 10 | On weekday, do you have fixed sleeping time? | I am sometimes absorbed in interesting books and stay up very late. | I do not stay up late for next morning. | I always sleep regular time. |

Fig.11

| 11 | Do you vary commuting manner? | I slightly change commuting time, way or train. | Commuting time, way and train are usually unchanged. | I feel anxiety if the commuting time, way or train is changed. |
|---|---|---|---|---|
| 12 | Do you cleave to job, position, many? | I am interested in, but not absolutely. | I am not interested. | They are proposes of my life and I cleave to them very much. |
| 13 | Do you love someone? | I seriously loved before or I love now seriously. | I want to love seriously but have no chance. | I am interested in women but I have never loved before. |
| 14 | Do you maintain small animal such as dog, cat, bird? | I take care of it and I feel it pretty. | I have it and feel it pretty, but care is troublesome. | I am not interested. |
| 15 | Do you watch flower? | Flower is beautiful, and I rear flower or go to see flower. | Flower is beautiful but I do not rear or go to see flower. | I am not interested. |

[Point of evaluation]

A: sensibility concerning communication with family (1-7)

B: sensibility concerning hobby and entertainment (8-9)

C: sensibility concerning communication with community (10-13)

D: sensibility concerning contact with nature (14-15)

Fig.12

1.2 In workplace

| | | | |
|---|---|---|---|
| 1 | Do you have company in workplace? | I positively find company, and contract a friendship with them. | I minimize company. | I do not like company. |
| 2 | Do you contact a friendship with boss or elder? | I show myself as it is, and I can contact a friendship even without workplace. | Company is troublesome. | I rather sell myself. For example, I never forget making a present gift of lantern festival or end of year. |
| 3 | Do you contact a friendship with subordinate? | Subordinates often call for me to go on pleasure or ask me advise. | Subordinates seldom call for me to go on pleasure or ask me advise. | Subordinates never call for me to go on pleasure or ask me advice. |
| 4 | Is your success achieved by team work? | Success largely depends on subordinates and my boss, but not failure. | Success credit goes to me, and failure goes to subordinates sometimes. | Success credit goes to me, and failure goes to subordinates. |
| 5 | Do you respect subordinates? | I educate and make environment so that subordinates have autonomy and identity. | Subordinates totally obeying me leave me wanting for more. | I like subordinates totally obeying me but do not like subordinates retorting me. |
| 6 | Do you have jealous on advance in office or promotional transfer of fellow or subordinates? | I pay no attention to advance in office or promotional transfer of fellow or subordinates. | Sometimes I have jealous on advance in office or promotional transfer of fellow or subordinates. | I always have jealous on advance in office or promotional transfer of fellow or subordinates. |
| 7 | Do you want to make workplace better and comfortable? | I positively improve not only workplace but also work itself. | I improve not only workplace but also work itself. | I do my own job, but I am not interested in improvement of workplace. |

Fig.13

| | | | |
|---|---|---|---|
| 8 | Do you have new song to sing or secret accomplishment for party of business scene? | I sing or show accomplishment for party of business scene. | I seldom sing or show accomplishment for party of business scene. | I do not sing or show accomplishment for party of business scene. |
| 9 | Are you forging ahead with creative job? | Idea for development or sales method of new product comes out and I enjoy. | I manage to do development or sales method of new product if I must do. | Idea does not come out, and I avoid such a job. |
| 10 | Do you draw the line between job and play? | I often travel with my family by taking continuous holiday. | For many years, I have not taken continuous holiday for travelling with my family. | I seldom take continuous holiday for travelling with my family. |

[Point of evaluation]

A: sensibility concerning contact with fellow, boss, subordinates (1-5)

B: sensibility concerning improvement of atmosphere (6-7)

C: sensibility concerning relationship with job (8-10)

Fig.14

2. Full-time homemaker 2.1 In daily life

| | Question | Group1 | Group2 | Group3 |
|---|---|---|---|---|
| 1 | Can you have a joke with your husband of family? | I can make naturally. | I intentionally make. | I seldom make. |
| 2 | Do you compliment your husband? | I can compliment naturally. | I sometimes compliment. | I seldom compliment. |
| 3 | Do you speak gently to your children? | I do not graum but speak gently to my children. | I graum but also speak gently to my children. | I often graum but never speak gently to my children. |
| 4 | Can you advise appropriately for your family? | Usually I am gentle to family but sometimes advise strictly. | I often graum for family but also advise. | I often graum for family but do not advise. |
| 5 | Do you like music and painting? | I sometimes appreciate with my husband. | I sometimes talk with my husband about them. | I am not interested. |
| 6 | Do you go Karaoke? | I sometimes go with my husband or family. | I have been to Karaoke with my husband or family for a few times. | I do not like singing. |
| 7 | Do you enjoy holiday with your family? | I go driving or travel with my family because I am unloaded. | I do not like, but I go with my family for service. | I take a rest at home and this is the best. |
| 8 | Do you play Igo, Shougi, Hanafuda, play cards or majan? | I have confidence. | I do but for service. | I do not like game or bet. |
| 9 | Do you play musical instrument, draw painting, enjoy sports such as baseball, golf, ski? | I have something that I can be enthusiastic. | If I have time, I want to do something. | I am not interested in hobby or sports. |

Fig. 15

| | | | | |
|---|---|---|---|---|
| 10 | On weekday, do you have fixed sleeping time? | I am sometimes absorbed in to interesting books and stay up very late. | I do not stay up late for next morning. | I always sleep regular time except special time. |
| 11 | Do you contact a friendship with friend well? | I contact a friendship with friend and I enjoy it. | I contact a friendship with friend but only outward. | I do not contact a friendship. |
| 12 | Do you pay attention to appearances or reputation? | I do not care about appearances or reputation. | I care about appearances or reputation more than necessary. | Most of my life is influenced by appearances or reputation. |
| 13 | Do you have pride for being official of PTA or block club? | I do not have pride for being official of PTA or block club. | I slightly have pride for being official of PTA or block club | I do really have pride for being official of PTA or block club. |
| 14 | Do you maintain small animal such as dog, cat, bird? | I take care of it and I feel it pretty. | I have it and feel it pretty, but care is troublesome. | I am not interested. |
| 15 | Do you watch flower? | Flower is beautiful, and I rear flower or go to see flower. | Flower is beautiful but I do not rear or go to see flower. | I am not interested. |

[Point of evaluation]

A: sensibility concerning communication with family (1-7)

B: sensibility concerning hobby and entertainment (8-9)

C: sensibility concerning communication with community (10-13)

D: sensibility concerning contact with nature (14-15)

Fig.16

2.2 Concerning housework

| | Question | Group1 | Group2 | Group3 |
|---|---|---|---|---|
| 1 | Do you enjoy nice food? | I very much like eating nice food, I like eating outside. | I rather like eating nice food, I like eating out. | I am not interested in eating nice food. |
| 2 | Are you a good cook? | Dishes I cooked gains reputation and people ask recipe to me. | People sometimes say you are a good cook. | No one say you are a good cook. |
| 3 | Do you cook originally or refer to book? | I can cook various dishes, and there are many original dishes. | Sometimes I can cook based on book, and sometimes originally. | I have never cook originally, and I cook always based on book. |
| 4 | Do you cook suitably for season or menu? | I cook seasonal dishes taking nutrition into account. | I use bargain but I also take season and nutrition into account. | I don't pay attention to season and nutrition, and I cook only with bargain. |
| 5 | Is washing troublesome? | I challenge heavy spot stain removing. | I do not like washing taking time and labor, but I do washing by myself. | Washing is troublesome, and I seldom do washing by myself. |
| 6 | Are you interested in new detergent or medicine? | I am interested in new detergent and chemicals. | I am a little bit interested in new detergent and chemicals. | I am not interested in new detergent and chemicals. |
| 7 | Is room cleaning troublesome? | I clean up room very nook and corner and I enjoy. | I only clean where I can see, and I clean room because I must do. | Cleaning is troublesome and I seldom clean. |
| 8 | Can you manage a family budget? | I manage all of a family budget by myself. | Husband helps me manage a family budget. | I leave a family budget to husband. |

Fig.17

| | | | | |
|---|---|---|---|---|
| 9 | Do you obtain information from magazine, TV and the like? | I am sensitive to information, and I have wide knowledge and information. | Although not positively, I obtain knowledge and information in my own way. | I do not obtain information from newspaper, magazine or TV, and I am not interested. |
| 10 | Do you have confidence in living alone without recourse of others? | I have confidence without recourse of husband or relative. | I have confidence in living alone although I feel anxiety. | I can not live without recourse of others. |

[Point of evaluation]

A: sensibility concerning cooking (1-4)

B: sensibility concerning cleaning and washing (5-7)

C: sensibility concerning other living matters (8-10)

Fig.18

DEMENTIA TEST APPARATUS, DEMENTIA TEST SERVER, DEMENTIA TEST CLIENT AND DEMENTIA TEST SYSTEM

FIELD OF THE INVENTION

The present invention relates to a dementia test apparatus for testing a dementia degree of a testee, a dementia test system, a dementia test server constituting the dementia test system, and a dementia test client.

DESCRIPTION OF THE RELATES ART

We are at the head of the 21st century and in Japan, a state in which graying and declining birthrate are simultaneously in process will be continued. The number of senior citizens requiring care is increased and the number of people of age bracket giving care is reduced, and in such a state, care for maintaining health of senior citizen is a national important problem.

Especially, senile dementia is a difficult problem to be solved because if the dementia degree is worsened, it is impossible to recover and great labor is required for the care due to the nature of the dementia. The Ministry of Health and Welfare estimates that future transition of dementia is 7.2% (11,560,000) of senior citizens of 65 years old or older in 2000, and 8.1% or more (2,260,000) in 2010.

On the other hand, according to recent researches, it becomes apparent that it is possible to prevent or recover the dementia by carrying out rehabilitation or training at relatively light degree of dementia. However, in the case of light dementia, there is no problem for daily life, and it is difficult to find the dementia.

SUMMARY OF THE INVENTION

The present invention has been accomplished in view of the above circumstances, and it is an object of the invention to provide a dementia test apparatus for testing a dementia degree of a testee, a dementia test system, a dementia test server constituting the dementia test system, and a dementia test client which are effective for ready detection of the initial sign (initial dementia) of the senile dementia.

A first dementia test system of the present invention achieving the above object comprises:

an answer obtaining section for obtaining an answer of a testee to a dementia degree test chart which requires a plurality kinds of judgements at the same time and obtains an answer in such a form that correction of judgement is objectively judged; and a dementia degree test section for testing a dementia degree indicative of a degree of dementia of the testee based on the answer obtained by the answer obtaining section.

A function of judgment of a human is controlled by a frontal lobe of a brain. The dementia is variously classified depending upon a cause of generation or the like. It is said that the most popular senile dementia (or obsolete dementia) is caused by hypofunction of the frontal lobe. To check the judgement by the frontal lobe function, it is found that a test requiring a plurality of judging force at the same time is effective. For example, in a "character pick-up" test which will be explained later, two operations, i.e., an operation to pick up characters such as "a", "b", "c", "d", "e", and an operation to understand contents of sentences thereof are carried out at the same time.

In the conventional "character pick-up" test, however, a counselor must attend the testee and judge to what degree the testee understands the meaning of the sentences, and this is not suitable of a dementia test for many people who are not aware of the dementia.

In the dementia test apparatus of the present invention, the dementia degree test chart which requires a plurality kinds of judgements at the same time and obtains an answer in such a form that correction of judgement is objectively judged is employed. An answer of the testee to the dementia degree test chart is obtained, and the dementia degree is tested based on the answer. By using the dementia test apparatus, it is possible to find the dementia earlier.

In the first dementia test apparatus of the present invention, it is preferable that the apparatus further comprises a chart storing section for storing the dementia degree test chart, and a chart display section for displaying the dementia degree test chart.

In the dementia test apparatus of the present invention, the testee's answer may be read in using an OCR (Optical Card Reader) or an operator may input the answer using a keyboard, but if the dementia degree test chart is stored and it is displayed as described above, the answer obtaining section can be constituted such that the testee himself or herself answers while receiving the test, and the apparatus can conveniently be handled.

The first dementia test apparatus of the present invention, when a plurality of testees are divided into a plurality of groups based on a predetermined criterion, may comprises a statistic storing section for storing a statistic processing result of answer of the testees in each of the groups, wherein the dementia degree test section tests a position in the statistic processing result of the answer to the dementia degree test chart of a current testee obtained by the answer obtaining section.

Here, examples of the "predetermined criterion" are "age-specific criterion" in which testees are separated based on age or "gender-specific and age-specific criterion". However, the invention is not limited to them, such criterion may simply be "gender-specific criterion", and the testees may be classified according to circumstances or climate, or disease, and the invention is not limited to a specific criterion.

As described above, the statistic processing result is stored, and a position with respect to the statistic result of the current testee is tested, and the dementia degree of the testee may be tested.

The first dementia test apparatus of the present invention may further comprise a dementia degree storing section for storing a relationship between the answer to the dementia degree test chart and a dementia degree, wherein the dementia degree test section refers to the dementia degree storing section, and tests a dementia degree of the current testee from the answer to the dementia degree test chart of the current testee obtained by the answer obtaining section.

In this manner, the dementia degree of the testee may be tested.

It is preferable that the first dementia test apparatus of the present invention further comprises a result display section for displaying a dementia degree test result obtained by the dementia degree test section.

By providing the result display section, it is possible to immediately and easily confirm the dementia degree of the testee.

It is preferable that the first dementia test apparatus of the present invention further comprises a test-allowability judging section for allowing or prohibiting a test-requiring person depending whether a predetermined time has been elapsed after the test-requiring person received the test last time.

This is because that if the testee receives the test frequently, there is a possibility that the testee becomes used to the test, and precise test can not be carried out.

A second dementia test apparatus of the present invention achieving the above object comprises:

an answer obtaining section for obtaining an answer of a testee to both a dementia degree test chart which requires a plurality kinds of judgements at the same time and obtains an answer in such a form that correction of judgement is objectively judged, and a dementia factor degree test chart comprising a combination of a plurality of question concerning sensibility and a plurality of answers alternatively selected from questions prepared for each of the former questions; and a dementia degree test section for testing a current degree of dementia indicative of dementia of the testee and for estimating transition of future dementia degree of the testee based on an answer obtained by the answer obtaining section.

In the second dementia test apparatus of the present invention, in addition to the dementia degree test chart for objectively testing the judgement by the frontal lobe employed also in the first dementia test apparatus, the dementia factor degree test chart is further employed. As described above, the dementia factor degree test chart is related to the sensibility, and judges how much the right-brain is used in daily life.

The main cause of dementia is hypofunction of the frontal lobe. If the frontal lobe is always used in the daily life, the frontal lobe is activated correspondingly, and dementia is not caused easily. The frontal lobe can be used by using the right-brain and by using the left-brain. In generally, the left-brain is not actively used with aging, and after about fifty years old, the right-brain is used mainly. Here, attention is paid to this point, and the dementia factor degree test chart testing how the right-brain controlling the sensibility is used (is not used) in daily life is employed. Like the dementia degree test chart, the dementia factor degree test chart is devised such as to obtain the answer in a manner capable of objectively evacuating.

The second dementia test apparatus of the present invention, the answers to the dementia degree test chart and the dementia factor degree test chart are obtained, and based on the obtained answers, the current dementia degree of the testee is tested and a transition of the future dementia degree is estimated, and this can be used for finding the initial dementia of the testee and for preventing the dementia.

Like the first dementia test apparatus, it is preferable that the second dementia test apparatus further comprises a chart storing section for storing the dementia degree test chart and a dementia factor degree test chart, and a chart display section for displaying the dementia degree test chart and the dementia factor degree test chart.

Furthermore, like the first dementia test apparatus, in the second dementia test apparatus of the invention, the testee's answer may be read in using an OCR (Optical Card Reader) or an operator may input the answer using a keyboard, but if the dementia degree test chart is stored and it is displayed, the answer obtaining section can be constituted such that the testee himself or herself answers while receiving the test, and the apparatus can conveniently be handled.

It is preferable that the second dementia test apparatus further comprises a statistic storing section, wherein a plurality of testees are divided into a plurality of groups based on a predetermined criterion, the statistic storing section stores a statistic processing result of answers of the testees to both the dementia degree test chart and the dementia factor degree test chart in each group, the dementia degree test section tests a current position of the statistic processing result of the answer of the current testee obtained by the answer obtaining section, and estimates a variation of a future position.

Here, like the first dementia test apparatus, examples of the "predetermined criterion" are "age-specific criterion" in which testees are separated based on age or "gender-specific and age-specific criterion". However, the invention is not limited to them, such criterion may be "gender-specific criterion", and the testees may be classified according to circumstances or climate, or disease, and the transition of dementia according to development of disease may be estimated.

Like the first dementia test apparatus, it is preferable that the second dementia test apparatus further comprises a result display section for displaying a dementia degree test result obtained by the dementia degree test section and a transition estimation result of the future dementia degree.

By using such a result display section, it is possible to immediately and easily confirm the dementia degree test result and the future dementia degree transition estimation result.

Like the first dementia test apparatus, it is preferable that the second dementia test apparatus further comprises a test-allowability judging section for allowing or prohibiting a test-requiring person depending whether a predetermined time has been elapsed after the test-requiring person received the test last time.

A testee will become used to the test but the above feature prevents incorrect result.

The basic idea of the present invention can be constituted as a server client system utilizing the Internet or the like. If the invention is constructed in this manner, a chance for testing the dementia degree can be supplied to more people, which is preferable. The server and client in the server client system is called dementia test server and dementia test client, respectively.

In a first dementia test system of the present invention, the idea of the first dementia test apparatus is applied to the server client system. That is, the first dementia test system of the invention comprising a dementia test server and a dementia test client connected to each other through a communication line, wherein the dementia test server comprises:
a chart storing section for storing a dementia degree test chart which requires a plurality kinds of judgement at the same time and obtains an answer in such a form that correction of judgement is objectively judged;
a chart sending section for sending the dementia degree test chart to the dementia test client;
an answer receiving section for receiving an answer to the dementia degree test chart from the dementia test client; and
a dementia degree test section for testing a dementia degree indicative of dementia degree of the testee based on the answer obtained by the answer obtaining section, and wherein the dementia test client comprises:
a chart receiving section for receiving the dementia degree test chart sent from the dementia test server;
a chart display section for displaying the dementia degree test chart obtained by reception in the chart receiving section;

an answer obtaining section for obtaining an answer to the dementia degree test chart displayed on the chart display section according to operation; and an answer sending section for sending an answer obtained by the answer obtaining section to the dementia test server.

The testee uses, for example, his or her personal computer as the dementia test client, and the testee can receive the test of his or her dementia degree.

In a second dementia test system of the present invention, the idea of the second dementia test apparatus mentioned above is applied to the server client system. That is, the second dementia test system comprises a dementia test server and a dementia test client connected to each other through a communication line, wherein the dementia test server comprises:

a chart storing section for storing both a dementia degree test chart which requires a plurality kinds of judgements at the same time and obtains an answer in such a form that correction of judgement is objectively judged, and a dementia factor degree test chart which comprises combinations of a plurality of questions concerning sensibility and a plurality of answers alternatively selected from questions prepared for each of the former questions;

a chart sending section for sending the dementia degree test chart and the dementia factor degree test chart to the dementia test client;

an answer receiving section for receiving an answer to the dementia degree test chart and the dementia factor degree test chart from the dementia test client; and a dementia degree test section for testing a dementia degree indicative of a current degree of dementia of the testee and for estimating transition of future dementia degree of the testee based on an answer obtained by the answer receiving section, and wherein the dementia test client comprises:

a chart receiving section for receiving both the dementia degree test chart which requires a plurality kinds of judgements at the same time and obtains an answer in such a form that correction of judgement is objectively judged, and a dementia factor degree test chart which comprises combinations of a plurality of questions concerning sensibility and a plurality of answers alternatively selected from questions prepared for each of the former questions sent from the dementia test server;

a chart display section for displaying the dementia degree test chart and the dementia factor degree test chart received by the chart receiving section;

an answer obtaining section for obtaining an answer to the dementia degree test chart and the dementia factor degree test chart displayed on the chart display section according to operation; and an answer sending section for sending the answer obtained by the answer obtaining section to the dementia test server.

In the second dementia test system also, the testee uses his or her personal computer as the dementia test client, and the testee can receive the test of his or her current dementia degree and receive estimation of future dementia degree transition.

A first dementia test server of the invention is preferable as a dementia test server in the first dementia test system, the first dementia test server comprising a dementia test server and a dementia test client connected to each other through a communication line, comprises:

a chart storing section for storing a dementia degree test chart which requires a plurality kinds of judgement at the same time and obtains an answer in such a form that correction of judgement is objectively judged;

a chart sending section for sending said dementia degree test chart to said dementia test client;

an answer receiving section for receiving an answer to said dementia degree test chart from said dementia test client; and a dementia degree test section for testing a dementia degree indicative of a degree of dementia of the testee based on the answer obtained by said answer obtaining section.

Here, the first dementia test server may further comprises a statistic storing section, wherein a plurality of testees are divided a plurality of groups based on a predetermined criterion, the statistic storing section stores a statistic processing result of answers to the dementia degree test chart in each group, the dementia degree test section tests a position of the statistic processing result of an answer of a current testee received by the answer receiving section.

The first dementia test server may further comprise a dementia degree storing section for storing a relationship between a dementia degree and an answer to the dementia degree test chart, wherein the dementia degree test section refers to the dementia degree storing section, and tests a dementia degree of the current testee from the answer of the current testee received by the answer receiving section.

It is preferable that the first dementia test server further comprises a result sending section for sending a dementia degree test result obtained by the dementia degree test section to the dementia test client.

It is preferable that the first dementia test server further comprises a test-allowability judging section for allowing or prohibiting a test-requiring person depending whether a predetermined time has been elapsed after the test-requiring person received the test last time.

A first dementia test client of the invention is preferable as a dementia test client in the first dementia test system, and the first dementia test client in a dementia test system comprising a dementia test server and a dementia test client connected to each other through a communication line, comprises:

a chart receiving section for receiving a dementia degree test chart which requires a plurality kinds of judgements at the same time and obtains an answer in such a form that correction of judgement is objectively judged sent from the dementia test server;

a chart display section for displaying a dementia degree test chart received by the chart receiving section;

an answer obtaining section for obtaining an answer to a dementia degree test chart displayed on the chart display section according to operation; and an answer sending section for sending an answer obtained by the answer obtaining section to the dementia test server.

Here, it is preferable that the first dementia test client further comprises a result receiving section for receiving a dementia degree test result obtained at and sent from the dementia test server by sending said answer to said dementia test server, and a result display section for displaying a dementia degree test result received by said result receiving section.

A second dementia test server of the invention is preferable as a dementia test server in the second dementia test system of the invention, and the second dementia test server comprising a dementia test server and a dementia test client connected to each other through a communication line, comprises:

a chart storing section for storing both a dementia degree test chart which requires a plurality kinds of judgement at the same time and obtains an answer in such a form that correction of judgement is objectively judged, and a dementia factor degree test chart comprising a combination of a plurality of question concerning sensibility and a plurality of answers alternatively selected from questions prepared for each of the former questions;

a chart sending section for sending both the dementia degree test chart and the dementia factor degree test chart to the dementia test client;

an answer receiving section for receiving an answer to the dementia degree test chart and the dementia factor degree test chart from the dementia test client; and dementia degree test section tests a dementia degree indicative of a current degree of dementia of a testee and estimates a transition of a future dementia degree based on the answer received by the answer receiving section.

Here, it is preferable that the second dementia test server further comprises a statistic storing section, when a plurality of testees are divided into a plurality of groups based on a predetermined criterion, for storing processing result of answers of the testees to both the dementia degree test chart and the dementia factor degree test chart in each group, wherein the dementia degree test section tests a current position of the statistic processing result of the answer of the current testee received by the answer receiving section, and estimates a variation of a future position.

Further, it is preferable that the second dementia test server further comprises a result sending section for sending a dementia degree test result obtained by the dementia degree test section and a transition estimation result of the future dementia degree to the dementia test client.

Further, it is preferable that the second dementia test server further comprises a test-allowability judging section for allowing or prohibiting a test-requiring person depending whether a predetermined time has been elapsed after the test-requiring person received the test last time.

A second dementia test client of the invention is preferable as a dementia test client in the second dementia test system, and the second dementia test client comprising a dementia test server and a dementia test client connected to each other through a communication line, comprises:

a chart receiving section for receiving both a dementia degree test which requires a plurality kinds of judgement at the same time and obtains an answer in such a form that correction of judgement is objectively judged, and a dementia factor degree test chart comprising a combination of a plurality of question concerning sensibility and a plurality of answers alternatively selected from questions prepared for each of the former questions;

a chart display section for displaying a dementia degree test chart and a dementia factor degree test chart received by the chart receiving section;

an answer obtaining section for obtaining answers to the dementia degree test chart and the dementia factor degree test chart displayed on the chart display section according to operation; and an answer sending section for sending an answer obtained by the answer obtaining section to the dementia test server.

Here, it is preferable that the second dementia test client comprises a result receiving section for receiving a transition estimation result of a future dementia degree and a dementia degree test result obtained from the dementia test server by sending the answer sent from the dementia test server to the dementia test server, and a result display section for displaying a dementia degree test result and a transition estimation result of a future dementia degree received by the result receiving section.

BRIEF DESCRIPTION OF THE DRAWINGS

FIG. 4 shows an example of a dementia degree test chart stored in a chart storing section.

FIG. 5 is a test chart of "character pick-up" test;

FIG. 6 shows an example of question concerning the "character pick-up" test in FIG. 5.

FIG. 11 shows an example of the dementia factor degree test chart.

FIG. 12 shows an example of the dementia factor degree test chart.

FIG. 13 shows an example of the dementia factor degree test chart.

FIG. 14 shows an example of the dementia factor degree test chart.

FIG. 15 shows an example of the dementia factor degree test chart.

FIG. 16 shows an example of the dementia factor degree test chart.

FIG. 17 shows an example of the dementia factor degree test chart.

FIG. 18 shows an example of the dementia factor degree test chart.

DESCRIPTION OF THE PREFERRED EMBODIMENTS

Hereinafter, embodiments of the present invention will be described.

Figure 1:
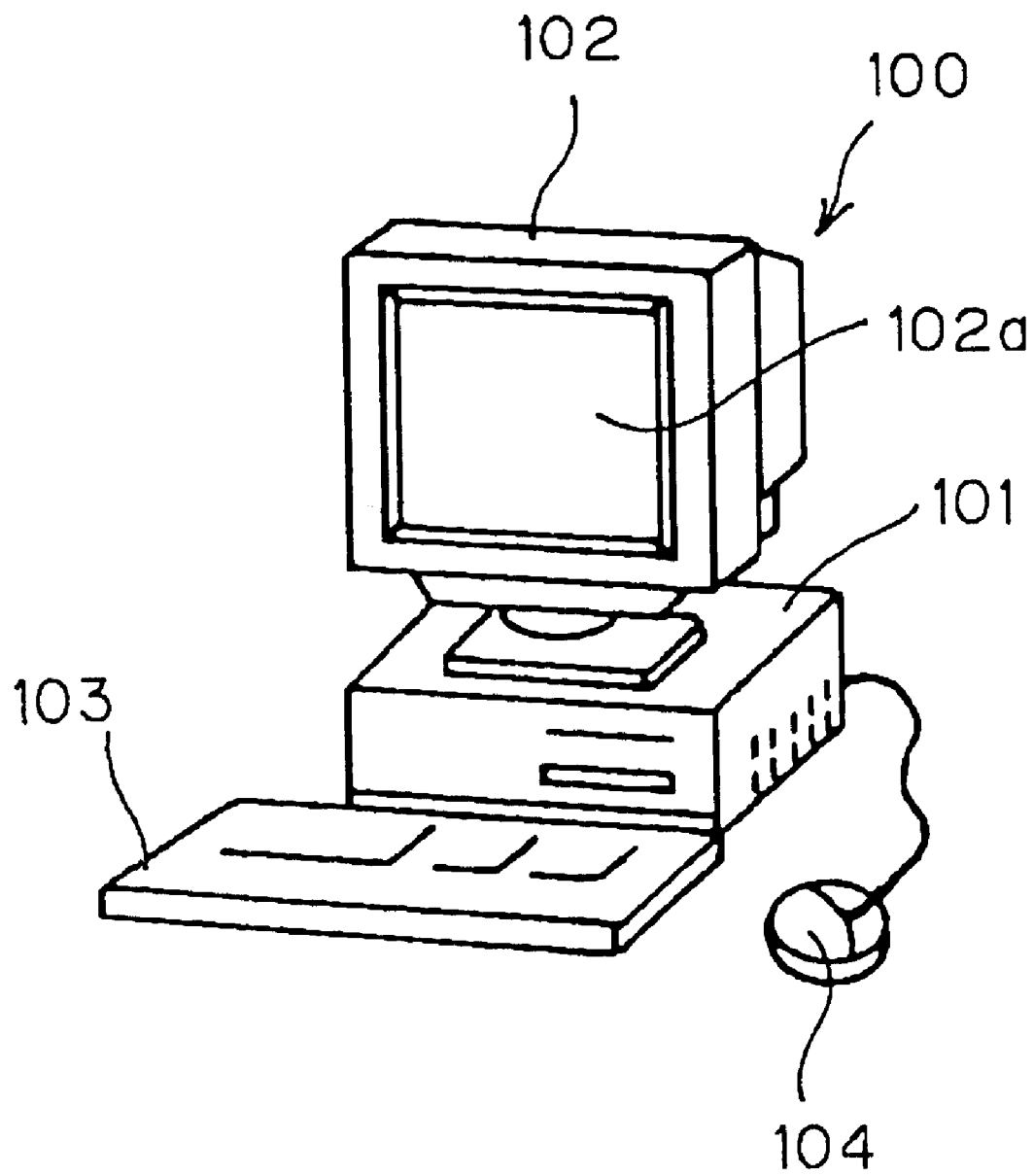
FIG. 1 is a perspective view of an outer appearance of a computer system operating as a dementia test apparatus according to an embodiment of the present invention.

FIG. 1 is a perspective view of an outer appearance of a computer system operating as a dementia test apparatus according to an embodiment of the present invention. A dementia test apparatus in an embodiment of the present invention is realized by a combination of hardware of the computer system 100 and software executed therein.

The computer system 100 comprises a body 101 having a CPU, a RAM memory, a magnetic disc, a communication board and the like therein, a CRT display 102 for displaying on a display screen 102a according to instructions from the body, a keyboard 103 for inputting instructions or character information by a testee or other operator, and a mouse 104 for inputting instructions according to an icon displayed on the display screen by designating an optional position thereon.

In the body 101, a CD-ROM drive for driving a CD-ROM 105 (see FIG. 2) is incorporated. The CD-ROM 105 can removably put in the drive.

In the CD-ROM 105, a dementia test program is stored, the CD-ROM 105 is inserted into the body 101, the dementia test program stored in the CD-ROM 105 is installed in the magnetic disc of the computer system 100 by the CD-ROM drive. If the dementia test program installed in the magnetic disc of the computer system 100 is started, the computer system 100 operates as an embodiment of the dementia test apparatus of the invention.

Figure 2:
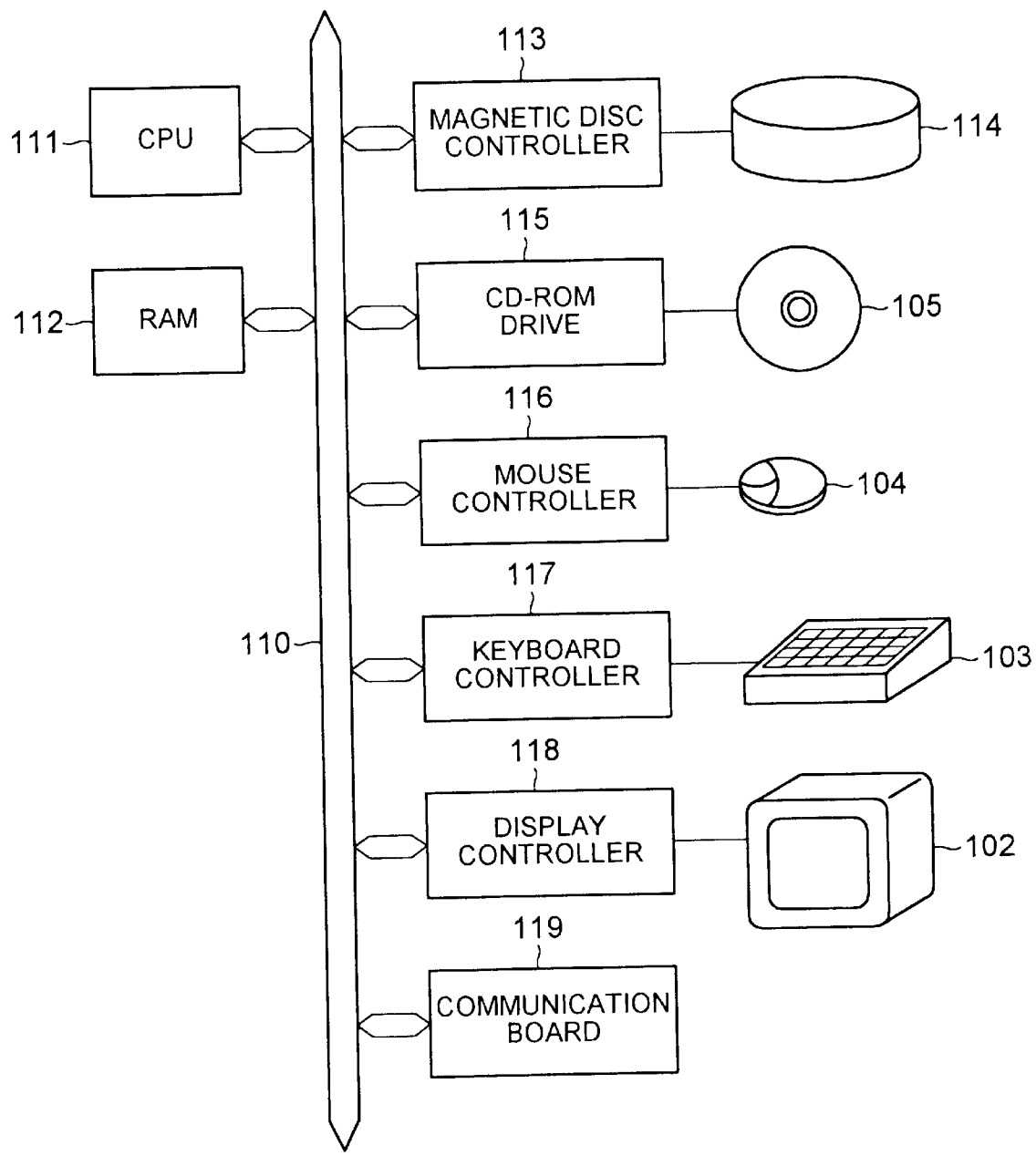
FIG. 2 shows a hardware structure of the computer system shown in FIG. 1.

FIG. 2 shows a hardware structure of the computer system 100 shown in FIG. 1.

In the drawing showing hardware structure, a central processing unit (CPU) 111, a RAM 112, a magnetic disc controller 113, a CD-ROM drive 115, a mouse controller 116, a keyboard controller 117, a display controller 118 and a communication board 119 are shown. These are connected to each other through a bus 110.

As explained with reference to FIG. 1, the CD-ROM 105 is put into the CD-ROM drive 115, and the CD-ROM drive 115 accesses the CD-ROM 105.

The communication board 119 is connected to a communication line. A test result of a testee carried out using the computer system is sent to a server (not shown) which accumulates data through the communication board 119, and the result is utilized for a progress observation of the testee and statistic processing concerning many testees.

FIG. 2 also shows a magnetic disc 114 accessed by the magnetic disc controller 113, a mouse 104 controlled by the mouse controller 116, a keyboard 103controlled by the keyboard controller 117, and the CRT display 102 controlled by the display controller 118.

Figure 3:
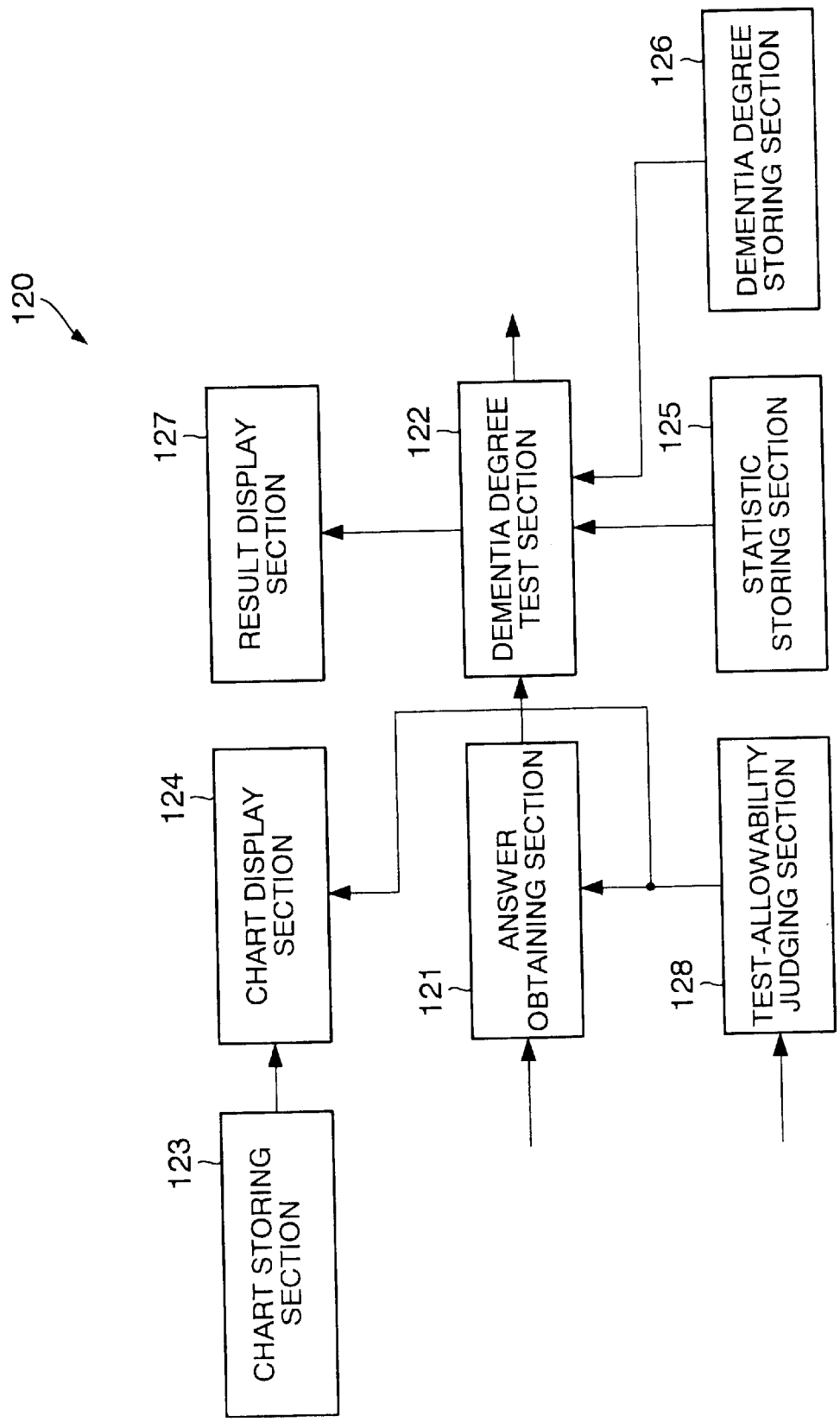
FIG. 3 is a functional block diagram of an embodiment of the dementia test apparatus of the invention realized when a dementia test program is executed in the computer system shown in FIGS. 1 and 2.

FIG. 3 is a functional block diagram of an embodiment of the dementia test apparatus of the invention realized when the dementia test program is executed in the computer system shown in FIGS. 1 and 2.

An answer obtaining section 121 shown in FIG. 3 constituting a dementia test apparatus 120 obtains an answer of a testee to a dementia degree test chart which requires a plurality kinds of judgements at the same time and obtains the answer in such a form that correction of judgement is objectively judged. As hardware, the keyboard 103 and the mouse 104 shown in FIGS. 1 and 2 correspond to the answer obtaining section 121.

A dementia degree test section 122 tests a dementia degree indicative of a degree of dementia of a testee based on the answer obtained by the answer obtaining section 121. As hardware, the magnetic disc 114 storing a program carrying out the test and the CPU 111 executing the program carrying out the test correspond to the dementia degree test section 122 and the like.

A chart storing section 123 stores a dementia degree test chart, and as hardware, the magnetic disc 114 and the like shown in FIG. 2 correspond to this. The dementia degree test chart stored in the chart storing section 123 is read out for testing the dementia degree, and is displayed on a chart display section 124. The CRT display 102 shown in FIGS. 1 and 2 functions as the chart display section 124 as hardware.

A plurality of testees are divided into a plurality of groups based on a predetermined criterion (in this embodiment, the criterion is age, and ages of the testees are divided into twenties, thirties, forties, . . . , on ten year base). A statistic storing section 125 stores a statistic processing result of answers (average value and distribution in this embodiment) of each the groups. The magnetic disc 114 functions as the statistic storing section 125 as hardware.

The dementia degree test section 122 utilizes the statistic processing result (average value and distribution on age-specific base in this embodiment) stored in the statistic storing section 125, and detects a position of an answer to the dementia degree test chart of the current testee obtained by the answer obtaining section 121 with respect to the statistic processing result.

A dementia degree storing section 126 stores a relationship between answer to the dementia degree test chart and the dementia degree, and the dementia degree test section 122 refers to the dementia degree storing section 126 to test the dementia degree of the current testee based on the answer of the testee to the dementia degree test chart obtained by the answer obtaining section 121. The magnetic disc 114 functions as the dementia degree storing section 126 as hardware.

A result display section 127 displays a dementia degree test result obtained by referring to the statistic storing section 125 or the dementia degree storing section 126 by the dementia degree test section 122. Like the chart display section 124, the CRT display 102 functions as the result display section 127 as hardware.

Further, a test-allowability judging section 128 allows or prohibits test of a test-requiring person depending on whether a predetermined period(for example, three months) has been elapsed after the person received the last test.

The dementia test apparatus 120 shown in FIG. 3 is constituted in the above-described manner. For testing a dementia degree of a testee, the dementia test apparatus 120 functions as follows.

First, the test-requiring person inputs individual information such as name, age, sex and job. Once the person takes the test, an ID number may be informed to the testee so that if the testee inputs the ID number, other individual information is not required.

If such a individual information or ID number is input, the test-allowability judging section 128 searches whether the test-requiring person did not take the test for a predetermined time, for example, last three months. If the person took the test, the test-allowability judging section 128 controls so that a dementia degree test chart is not displayed on the chart display section 124 and an answer is not received by the answer obtaining section 121. This is because if a person took the test many times in a short time, there is no effect, besides the person becomes used to the test, erroneous result may come out.

When the test-requiring person takes the test for the first time, or when a predetermined period(for example, three months) has elapsed since the testee took the test, the person is allowed to take the test.

For taking the test, the dementia degree test chart is read out from the chart storing section 123 and is displayed on the chart display section 124. Before that, explanation of test method using the dementia degree test chart is displayed, and if start of the test is instructed by click of the mouse or the like, the dementia degree test chart is displayed. If a predetermined test time (for example, two minutes) elapses, the dementia degree test chart is erased from the screen.

In the test, the testee inputs answer to the dementia degree test chart by using the keyboard 103 or the mouse 104 constituting the answer obtaining section 121. The answer obtaining section 121 receives the input answer and sends the same to the dementia degree test section 122.

The dementia degree test section 122 refers to the statistic storing section 125 and the dementia degree storing section 126 to test the dementia degree based on the answer, and sends the test result to a result display section 127. The result display section 127 displays the dementia degree test result. The dementia degree test section 122 sends the dementia degree test result together with the individual information to a server (not shown) which accumulate data through the communication board 119 shown in FIG. 2. The data accumulation server utilizes the sent data, the progress observation of the testee and statistic processing concerning many testees as described above. The server periodically carries out statistic processing (average value and distribution on age-specific base), the statistic processing result is sent to the dementia test apparatus 120 shown in FIG. 3 from the server, and the contents of the statistic storing section 125 are renewed.

Hereinafter, concrete procedure in the dementia test apparatus 120 shown in FIG. 3 will be explained.

FIG. 4 shows an example of a dementia degree test chart stored in the chart storing section 123.

In this chart, many repetitive characters showing colors are arranged. The characters are shown with different colors. In the many characters, some of them meaning colors coincide with their own colors, and others meaning colors do not coincide with their own colors. For example, there are a plurality of "red" characters. Some of them are shown in red, and others are shown in different colors. The same can be said to other characters of "violet", "yellow", "blue" and the like.

Using this chart, it is checked whether color expressed by the character and color of the character coincide with each other one by one. That is, two kinds of judgements of a meaning of a character and color of the character are required. Such a test requiring two kinds of judgements at the same time is effective for testing the function of a frontal lobe. If the function of the frontal lobe is depressed, the dementia is caused.

In the case of the chart shown in FIG. 4, correction of an answer to each of the characters is objectively judged. Here, when a check result of each of the character is correct, +1 point is given, and when the result is not correct, −1 point is given.

For example, the dementia degree test chart shown in FIG. 4 is stored in the chart storing section 123. In the test, the dementia degree test chart is read out from the chart storing section 123 and displayed on the chart display section 124. The test is carried out in such a manner that a testee checks whether color expressed by a character coincides with color of the character using the mouse 104 or the like.

The idea of the dementia degree test chart shown in FIG. 4 can be applied to other languages such as Japanese. For example, characters meaning Red, Green and Yellow, and color of the characters are combined to make the dementia degree test chart of English version.

FIG. 5 is a test chart of "character pick-up" test.

Here, sentences having meanings are shown. A testee picks up characters "a", "b","c", "d", "e" while understanding the contents of the sentences. In this case also, two kinds of judgements of the testee, i.e., understanding of the contents and judgement of an appearance of specific character are required.

FIG. 6 shows an example of question concerning the "character pick-up" test in FIG. 5.

The questions shown in FIG. 6 is a screen displayed on the chart display section 124 after the completion of "character pick-up" test. The questions constitute the dementia degree test chart of the present invention together with the "character pick-up" test shown in FIG. 5.

FIG. 6 shows not only the questions, but also a grade result of the "character pick-up" test carried out immediately before the questions. Here, scores are calculated on the basis that when an answer is correct, 1 point is added, and incorrect, for example, −1 point is added, and when no answer, 0 point is added and also scores of the questions is added up.

The questions shown in FIG. 6 can be answered with ○ or ×, and understanding degree of content can be objectively grasped. Scores to the questions are calculated on the bases, for example, 2 points are added per one correct answer.

The dementia degree test chart shown in FIG. 4 or 5 and 6 is displayed on the chart display section 124 of the dementia test apparatus 120. If an answer of a testee to the chart is input in the answer obtaining section 121, the input answer is input to the dementia degree test section 122. In the dementia degree test section 122, the statistic storing section 125 or the dementia degree storing section 126 is referred to based on the answer as described above, and the dementia degree of the testee is tested. A test result is displayed on the result display section 127.

Figure 7:
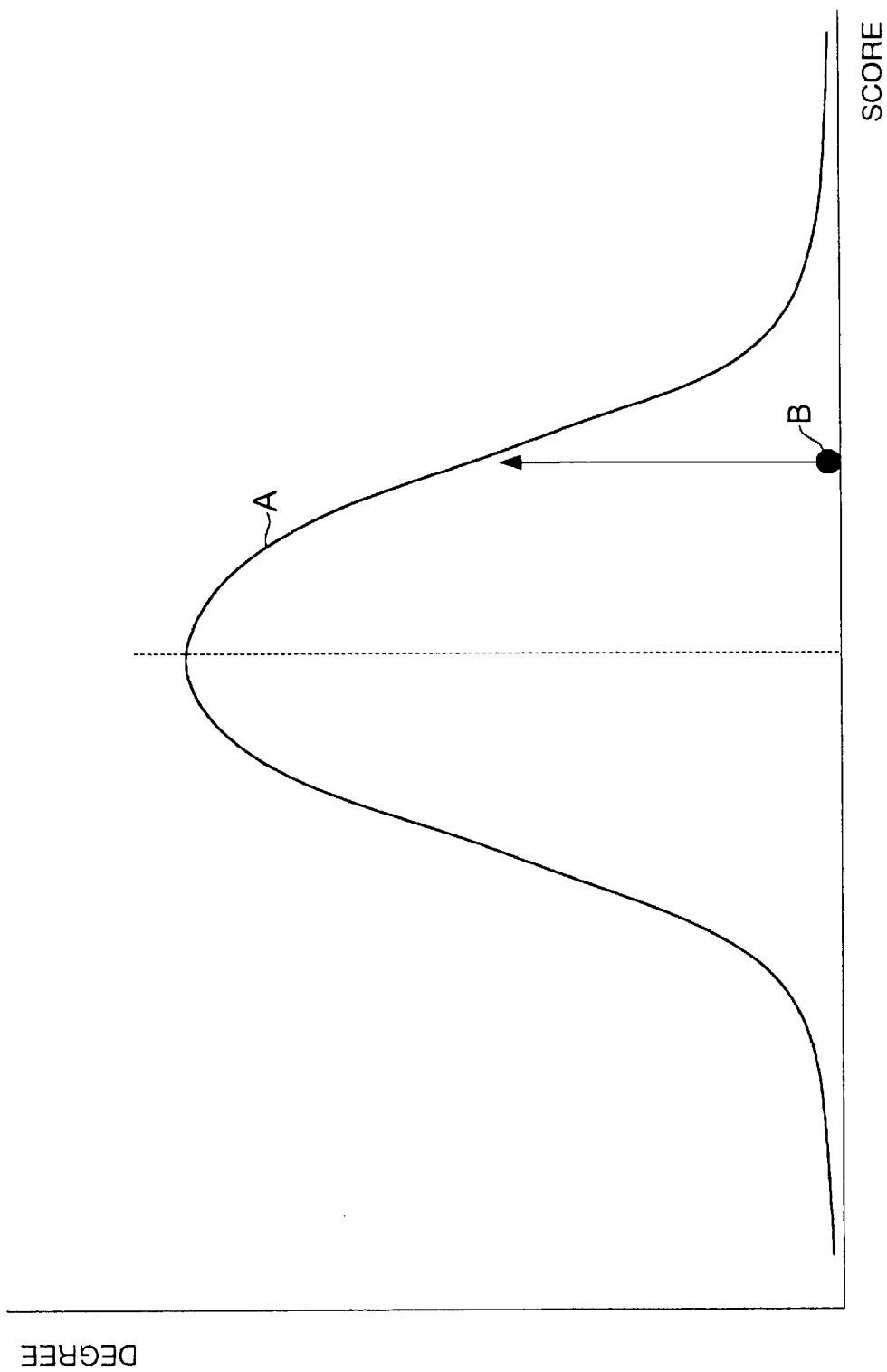
FIG. 7 shows an example of display of a dementia degree test result displayed on a result display section.

FIG. 7 shows an example of display of a dementia degree test section result displayed on a result display section 127. A lateral axis shows a score, and a vertical axis shows a degree.

In the statistic storing section 125, averages and distributions of last many testees are stored in an age-specific manner. From averages and distributions of each age, those of age of a current testee are read out, a histogram A shown in FIG. 7 indicative of score of the age of the testee is formed, and it is checked where a score B of the testee is located in the age.

The testee looks the test result shown in FIG. 7 displayed on the result display section 127, and the testee can objectively know his or her own dementia degree. A testee can access last test results and compare with the current test result.

Although FIG. 7 only shows the histogram A and the score B of the testee, a numeric value or explanation may be shown for indicating a dementia degree of the score B of the testee.

Figure 8:
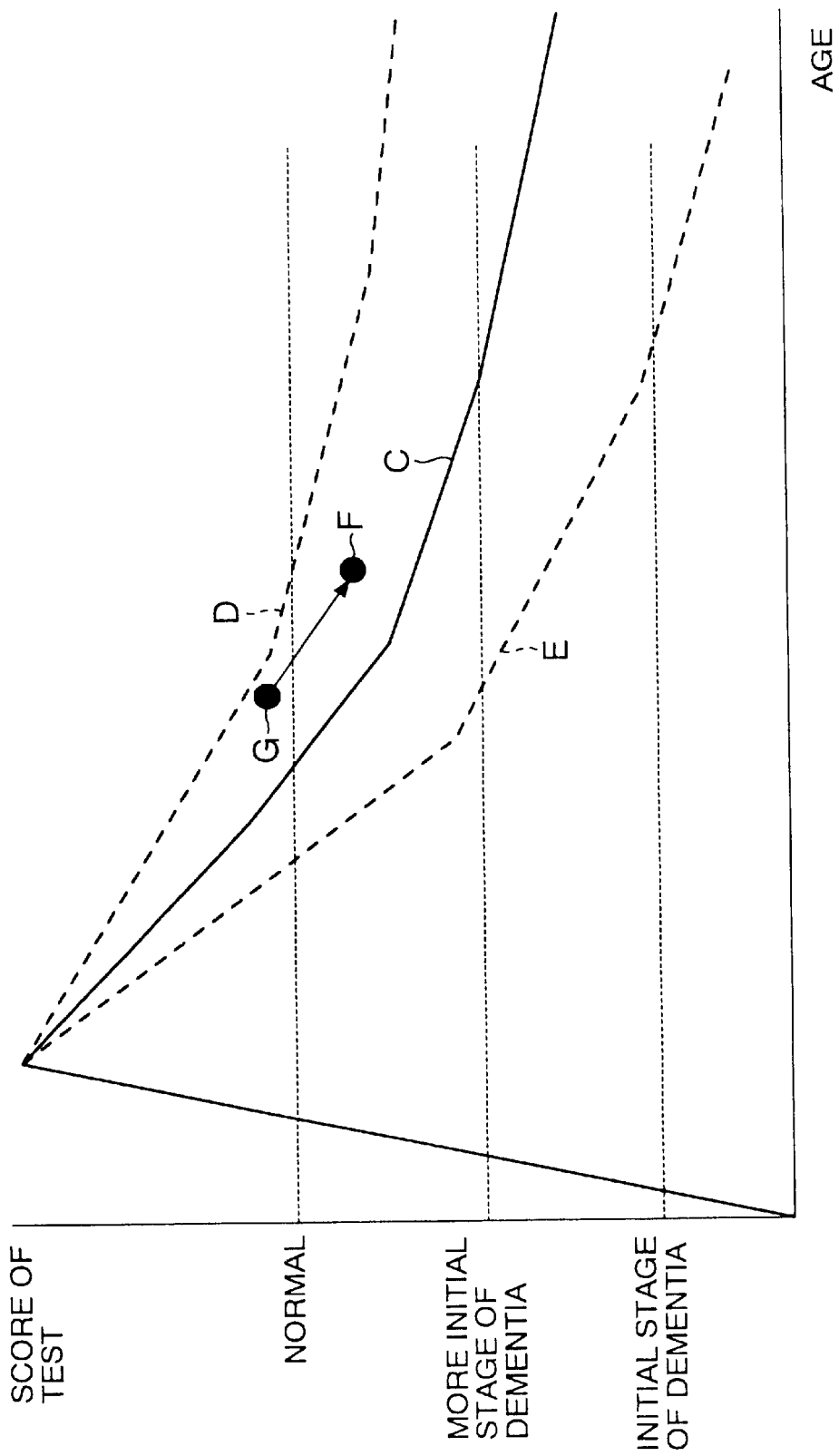
FIG. 8 shows another example of display of the dementia degree test result displayed on the result display section.

FIG. 8 shows another example of display of the dementia degree test result displayed on the result display section 127. Here, a lateral axis shows age of a testee, and a vertical axis shows a score of a test.

A relationship between a score to the dementia degree test chart and a dementia degree as shown in FIG. 8 is stored in the dementia degree storing section 126.

In the dementia degree storing section 126, an average value C in each age, and upper and lower limit values D and E which can be regarded as being normal on that age are stored.

In the dementia degree test section 122, it is tested which dementia degree a testee is and whether the testee is normal as that age based on data stored in the dementia degree storing section 126 and age and score F of the testee. The testee looks a screen indicating the test result shown in FIG. 8, displayed on the result display section 127, and can easily know a level of his or her own. The testee can access last test results G and compare with the current test result.

Figure 9:
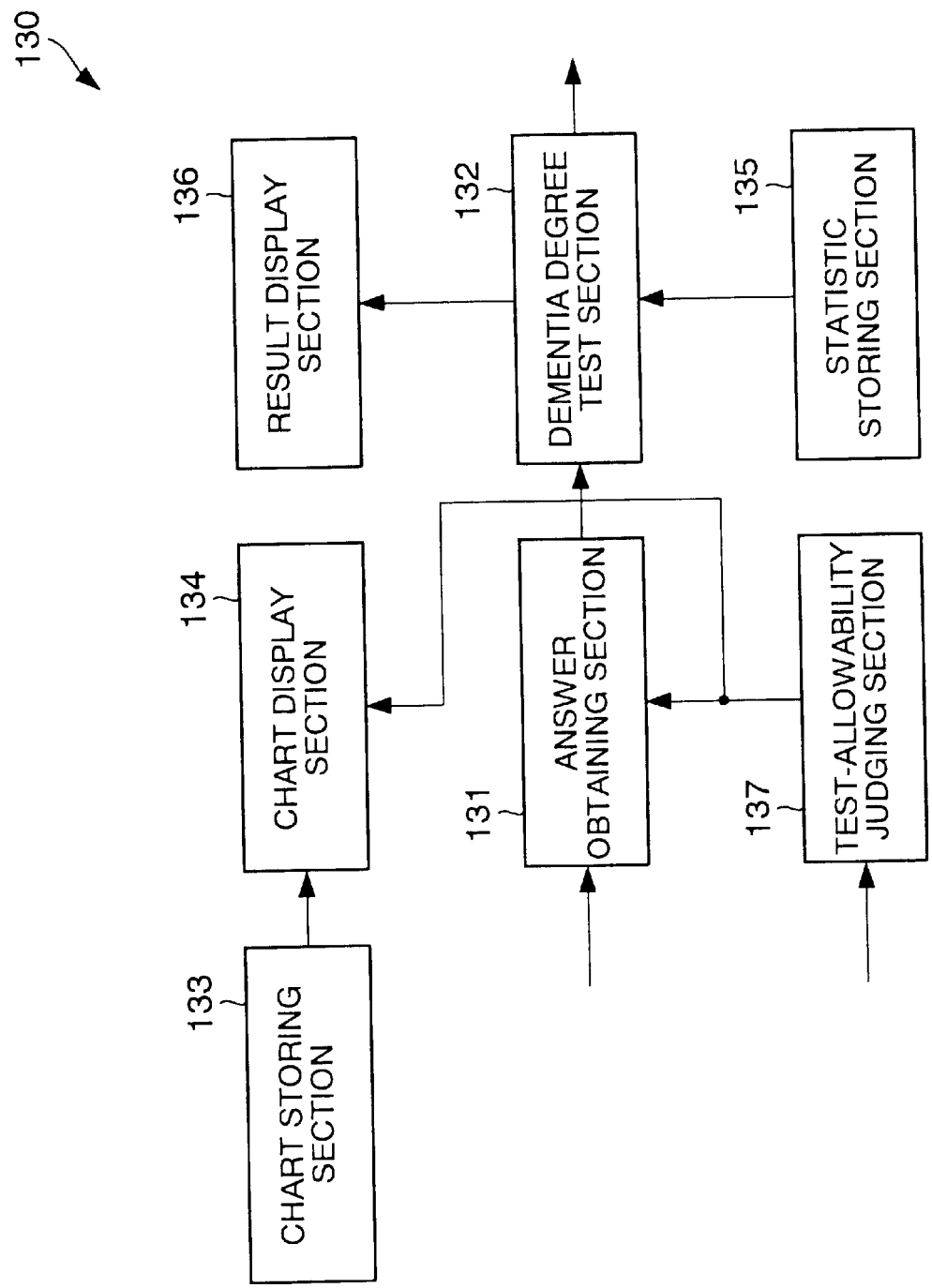
FIG. 9 is a functional block diagram of another embodiment of the dementia test apparatus of the invention realized when a dementia test program is executed in the computer system shown in FIGS. 1 and 2.

FIG. 9 is a functional block diagram of another embodiment of the dementia test apparatus of the invention realized when a dementia test program is executed in the computer system shown in FIGS. 1 and 2.

In an answer obtaining section 131 constituting a dementia test apparatus 130, answers of a testee to both a dementia degree test chart which is the same as that employed by the dementia test apparatus 120 and a dementia factor degree test chart comprising a combination of a plurality of questions concerning sensibility and a plurality of answers alternatively selected from questions prepared for each of the former questions are obtained. The keyboard 103 and the mouse 104 shown in FIGS. 1 and 2 correspond to the answer obtaining section 131 as hardware.

A dementia degree test section 132 tests a current dementia degree of a testee and estimate transition of a future dementia degree based on the answers obtained by the answer obtaining section. The magnetic disc 114 storing a program for carrying out the test and transition estimation and the CPU 111 or the like executing the program correspond to the dementia degree test section as hardware.

A chart storing section 133 stores the dementia degree test chart and the dementia factor degree test chart, and the magnetic disc 114 and the like shown in FIG. 2 corresponds to the chart storing section 133 as hardware. The dementia degree test chart and the dementia factor degree test chart stored in the chart storing section 133 are read out for testing the dementia degree and displayed on a chart display section 134. The CRT display 102 shown in FIGS. 1 and 2 functions as the chart display section 134 as hardware.

A plurality of testees are divided into a plurality of groups based on a predetermined criterion (in this embodiment, the criterion is age, and ages of the testees are divided into twenties, thirties, forties, . . . , on ten year base). A statistic storing section 135 stores a statistic processing result (least square approximation straight line in this embodiment as described later) of answers to the dementia degree test chart and the dementia factor degree test chart in each the groups. The magnetic disc 114 functions as the statistic storing section 135 as hardware.

A dementia degree test section 132 utilizes the statistic processing result (least square approximation straight line in this embodiment) stored in the statistic storing section 135, and tests a current position in the statistic processing result and estimates a variation of a future position of the current testee based on the answer to the dementia degree test chart and the dementia factor degree test chart of the current testee obtained by the answer obtaining section 131.

A result display section 136 displays the dementia degree test result and a future dementia degree transition estimation result obtained by referring to the statistic storing section 135 by the dementia degree test section 132. Like the chart display section 134, the CRT display 102 functions as the result display section 136 as hardware.

Further, a test-allowability judging section 137 allows or prohibit a test of a test-requiring person depending on whether a predetermined time (for example, three months) has elapsed since the test-requiring person took the test last time.

The dementia test apparatus 130 shown in FIG. 9 is constituted as described above, and for the test of a dementia degree of a testee, the dementia test apparatus 130 functions as follows.

First, the test-requiring person inputs individual information such as name, age, sex and job. Once the person takes the test, an ID number may be informed to the testee so that if the testee inputs the ID number, other individual information is not required.

If such a individual information or ID number is input, the test-allowability judging section 128 searches whether the test-requiring person did not take the test for a predetermined time, for example, last three months. If the person took the test, the test-allowability judging section 137 controls so that a dementia degree test chart is not displayed on the chart display section 134 and an answer is not received by the answer obtaining section 131. This is because if a person took the test many times in a short time, there is no effect, besides the person becomes used to the test, erroneous result may come out.

When the test-requiring person takes the test for the first time, or when a predetermined period, for example, three months have elapsed since the testee took the last test, the person is allowed to take the test.

For taking the test, the dementia degree test chart is read out from the chart storing section 133 and is displayed on the chart display section 134. Before that, explanation of test method using the dementia degree test chart is displayed, and if start of the test is instructed by click of the mouse, the dementia degree test chart is displayed. If a predetermined test time (for example, two minutes) is elapsed, the dementia degree test chart is erased from the screen.

In the test, the testee inputs answer to the dementia degree test chart using the keyboard 103 or the mouse 104 constituting the answer obtaining section 131. The answer obtaining section 131 receives the input answer and sends the same to the dementia degree test section 132.

Next, an explanation of a test method using the dementia factor degree test chart is displayed. Then, the dementia factor degree test chart is displayed by click of the mouse or the like. A testee sees the displayed dementia factor degree test chart and answers using the mouse or the like. The answer obtaining section 131 transfers the input answer to the dementia degree test section 132. The dementia degree test section 132 refers to the statistic storing section 135, tests a current dementia degree of the testee and estimates transition of a future dementia degree of the testee based on the answers. The dementia degree test result and the transition estimation result of the dementia degree are sent to the result display section 136, and the result display section 136 displays these results.

The dementia degree test section 132 sends the result together with the individual information of the testee to a server (not shown) which accumulate data through the communication board 119 shown in FIG. 2. The data accumulation server utilizes the sent data, the progress observation of the testee and statistic processing concerning many testees. The server periodically carries out statistic processing, the statistic processing result is sent to the dementia test apparatus 130 shown in FIG. 9 from the server, and the contents of the statistic storing section 135 are renewed.

Hereinafter, concrete procedure in the dementia test apparatus 130 shown in FIG. 9 will be explained.

Both the dementia degree test chart and the dementia factor degree test chart are stored in the chart storing section 133. The concrete example and handling of the dementia degree test chart are described above and thus, the explanation thereof is omitted here.

Figure 10:
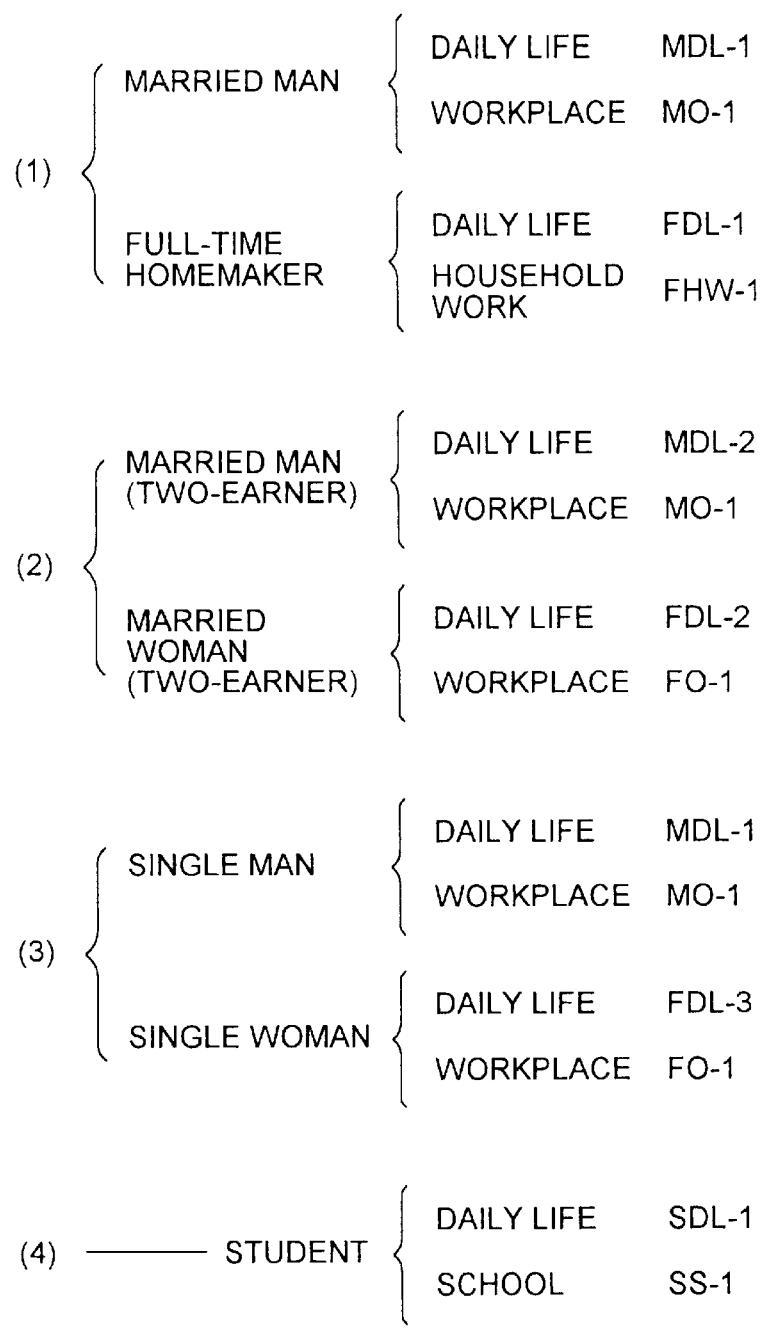
FIG. 10 shows classification of the dementia factor degree test chart.

FIG. 10 shows classification of the dementia factor degree test chart. FIGS. 11 to 18 show examples of the dementia factor degree test chart.

In the dementia factor degree test chart of the present embodiment, as shown in FIG. 10, there are prepared a total seven groups including "married man", "full-time homemaker", "married man (two-earner)", "married woman (two-earner)", "single man", "single women" and "student". Two kinds of dementia factor degree test charts, i.e., "daily life" and "workplace" (or "housework", "school") are prepared for each group.

FIGS. 11 and 12 show one example of a dementia factor degree test chart concerning "daily life" of the "married man". FIGS. 13 and 14 show one example of a dementia factor degree test chart concerning "workplace" of the "married man". FIGS. 15 and 16 show one example of a dementia factor degree test chart concerning "daily life" of the "full-time homemaker". FIGS. 17 and 18 show one example of a dementia factor degree test chart concerning "housework" of the "full-time homemaker". Dementia factor degree test charts for other groups are similarly formed, but they are not illustrated in the drawings.

These dementia factor degree test charts are for objectively estimating the degree of the activation of the right-brain and sensitivity in a daily life or in workplace.

In the test using the dementia factor degree test chart, for example, 1 group is +1 point, 2 group is 0 point and 3 group is −1 point, and these are added to make a score of a testee.

Dementia factor degree test charts of the dementia degree test charts shown in FIGS. 4, 5 and 6, and the dementia factor degree test charts shown in FIGS. 11 to 18 which are suited to the testee are sequentially displayed on the chart display section 134 of the dementia test apparatus 130 shown in FIG. 9, and the testee inputs answers to the charts by means of the answer obtaining section 131. The input answers is input in the dementia degree test section 132, as described above, this dementia degree test section 132 tests a current dementia degree of the testee and estimates transition of a future dementia degree of the testee. The current dementia degree test result and the transition estimation result of the dementia degree are sent to the result display section 136.

Figure 19:
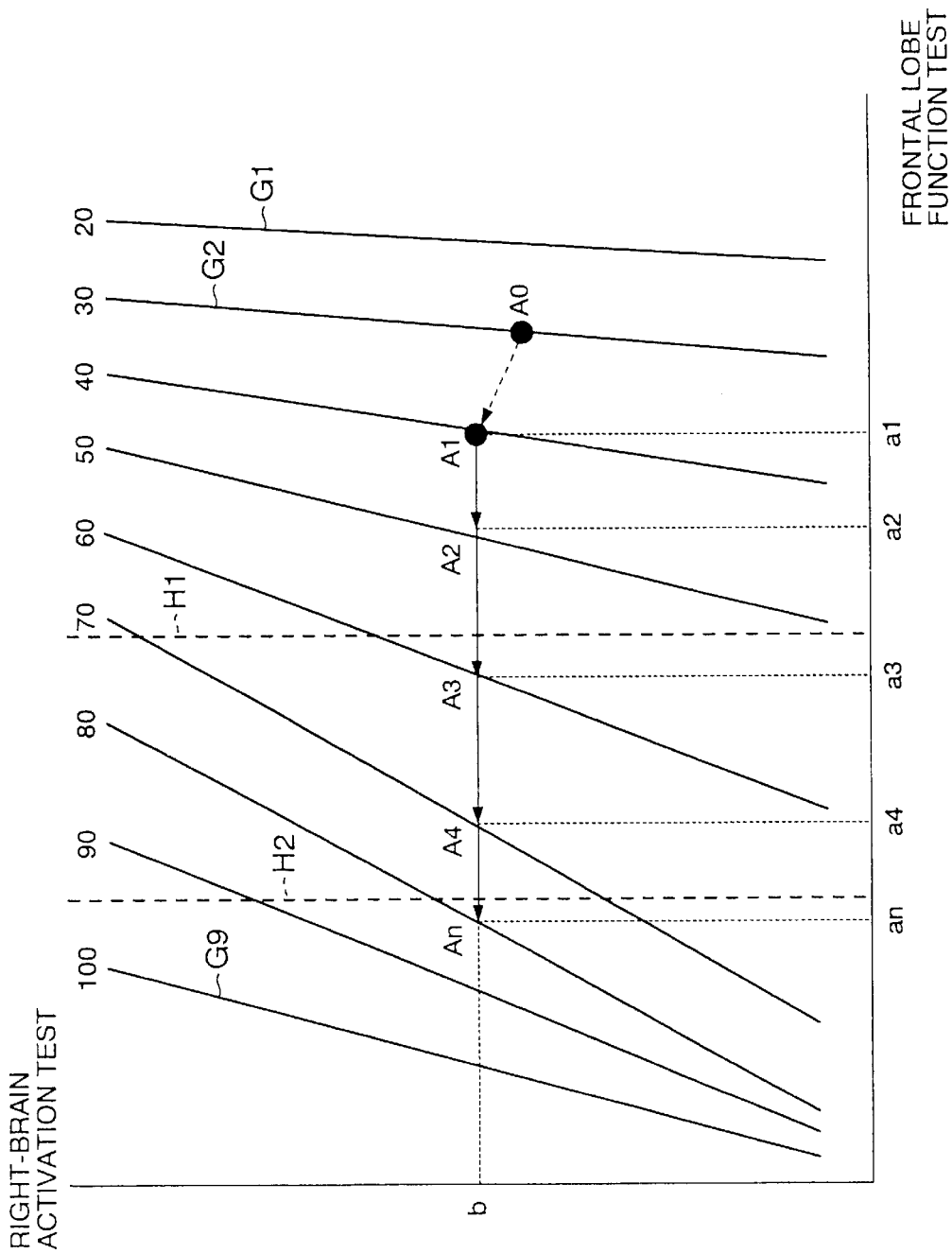
FIG. 19 shows an example of display on the result display section.

FIG. 19 shows an example of display on the result display section 136. A lateral axis of FIG. 19 shows a score of the frontal lobe function test using the dementia degree test chart, and a vertical axis shows a score of the right-brain activation test using the dementia factor degree test chart. The straight lines G1, G2, . . . , G9 respectively show minimum square approximate straight lines in each age of score distribution of many last testees in each age (twenties, thirties, . . . , centuries).

Two broken lines H1 and H2 extending vertically in FIG. 19 respectively show a dementia degree called "initial stage of dementia" and a dementia degree called "dementia".

These straight lines G1, G2, . . . , G9 show one example of statistic processing result of the invention, and are stored in the statistic storing section 135 shown in FIG. 9. These straight lines are read out by the dementia degree test section 132 to specify a position of the current testee in the result of the statistic procedure.

Here, if a score of the current testee in the frontal lobe function test using the dementia test chart is a1 and a score of the right-brain activation test using the dementia factor degree test chart is b, the testee is in the position A1. It is estimated that if the testee's living habit, i.e., the activity level of the right-brain is not changed, his or her position will be A2 after ten years, A3 after twenty years which means initial stage of dementia, A4 after thirty years, and An after forty years and the testee will be demented. Furthermore, changes of the positions can be shown by indicating the past position A0 of the testee.

From the test result of the right-brain activity degree using the dementia factor degree test chart, there is displayed an advice what degree the development of dementia can be suppressed by how the living habit is improved.

Figure 20:
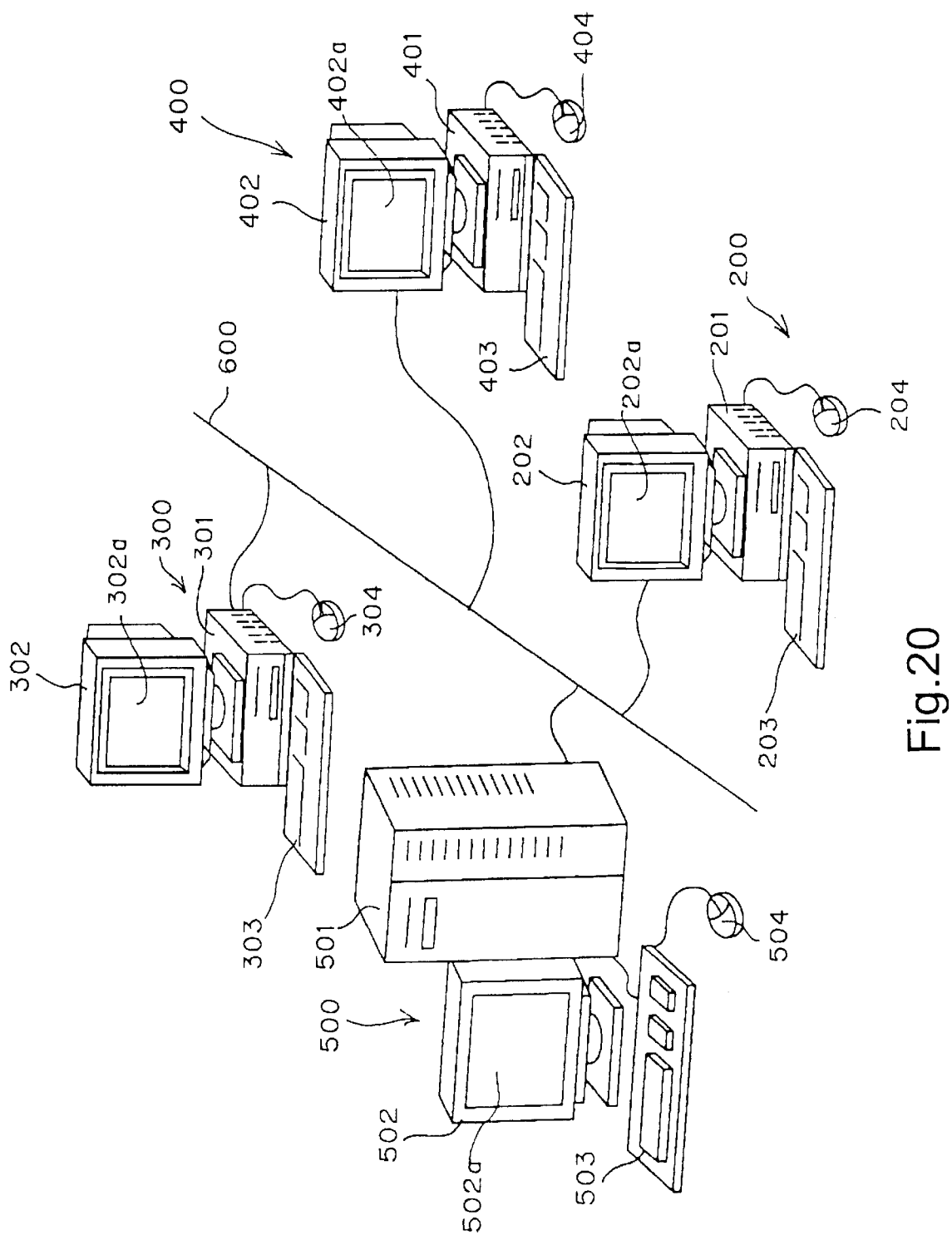
FIG. 20 shows a structure of a server client system operating as an embodiment of a dementia test system of the invention.

FIG. 20 shows a structure of a server client system operating as an embodiment of a dementia test system of the invention.

Here, three computer systems 200, 300, and 400 operating as a dementia test client and one computer system 500 operating as a dementia test server are shown. These systems are connected to each other through a communication line 600.

The computer systems 200, 300, 400 and 500 respectively include bodies 201, 301, 401 and 501 each having a CPU, a RAM, a magnetic disc, a communication board and the like therein, CRT displays 202, 302, 402 and 502 for displaying on display screens 202a, 302a, 402a and 502a according to instructions from the bodies, keyboards 203, 303, 403 and 503 for inputting instructions or character information by a testee or other operator, and mice 202, 302, 402 and 502 for inputting instructions according to icon displayed on a display screen by designating the mouse at an arbitrary position on the screen.

Hardware of each of the computer systems 200, 300, 400 and 500 is the same as that of the computer system 100 (see FIG. 2) shown in FIG. 1, and detailed explanation thereof is omitted.

Figure 21:
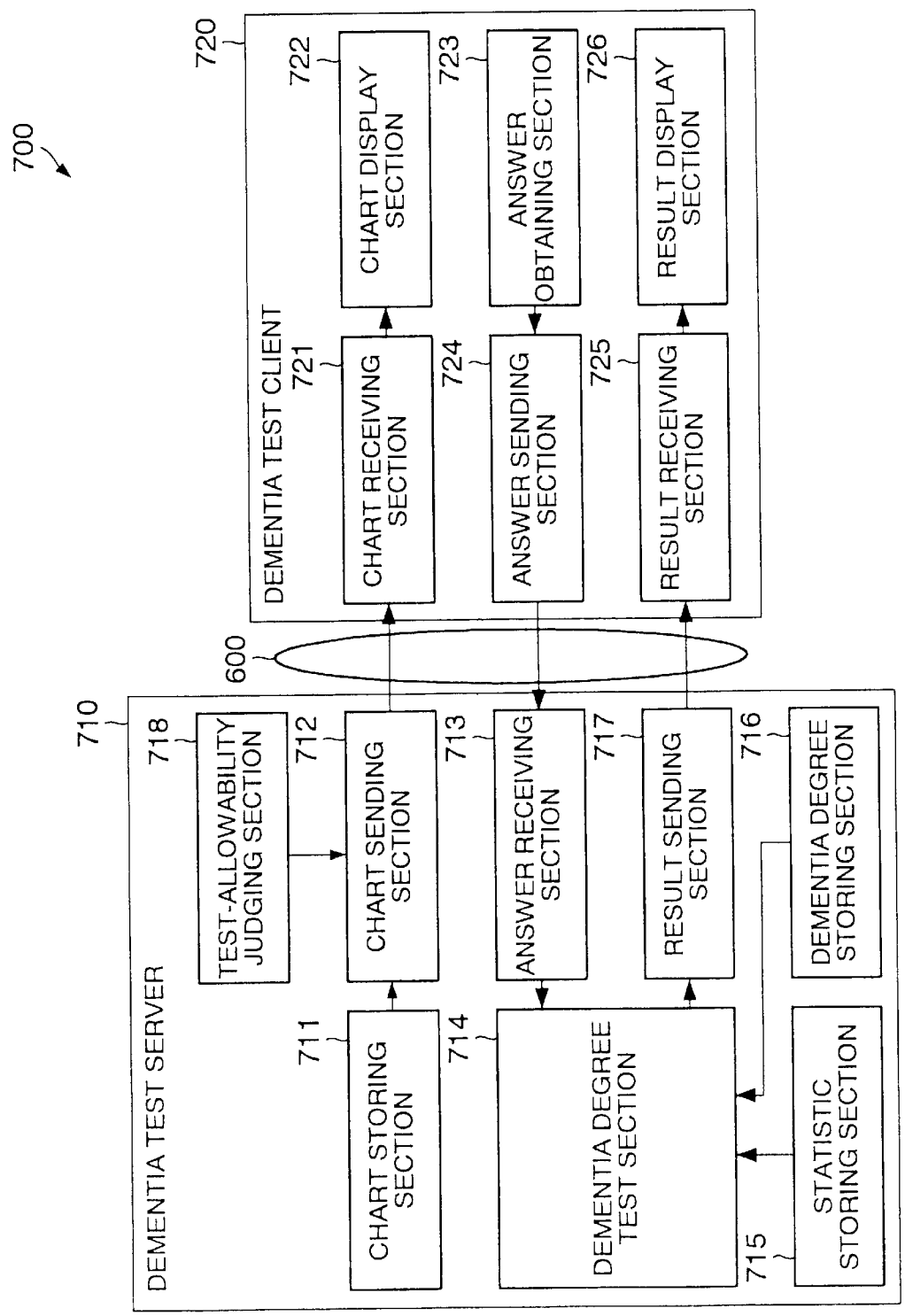
FIG. 21 is a functional block diagram of an embodiment of the dementia test system of the invention realized by the server client system shown in FIG. 20.

FIG. 21 is a functional block diagram of an embodiment of the dementia test system of the invention realized by the server client system shown in FIG. 20. Here, only one dementia test client is indicated as representative.

A dementia test system 700 comprises a dementia test server 710 and a dementia test client 720.

The dementia test server 710 constituting the dementia test system 700 comprises a chart storing section 711, a chart sending section 712, an answer receiving section 713, a dementia degree test section 714, a statistic storing section 715, a dementia degree storing section 716, a result sending section 717 and a test-allowability judging section 718.

Among them, the chart storing section 711, the dementia degree test section 714, the statistic storing section 715, the dementia degree storing section 716 and the test-allowability judging section 718 respectively function in the same manner as the chart storing section 123, the dementia degree test section 122, the statistic storing section 125, the dementia degree storing section 126, and the test-allowability judging section 128 constituting the above described dementia degree test apparatus 120 shown in FIG. 3. Therefore, explanation thereof is omitted. The test-allowability judging section 718 judges whether a test is allowed or prohibited based on individual information sent from the dementia test client 720. If the test was prohibited, sending of a dementia degree test chart from the chart sending section 712 is prohibited.

When the test was allowed, the chart sending section 712 reads out a dementia degree test chart from the chart storing section 711, and sends the same to the dementia test client 720. The answer receiving section 713 receives an answer to the dementia degree test chart sent from the dementia test client 720. The result sending section 717 sends the dementia degree test result obtained by the dementia degree test section 714 to the dementia test client 720. The communication board (see FIG. 2) of the computer system functioning mainly as the dementia test server 710 corresponds to these as hardware.

The dementia test client 720 constituting the dementia test system 700 comprises a chart receiving section 721, a chart display section 722, an answer obtaining section 723, an answer sending section 724, a result receiving section 725 and a result display section 726. Among them, the chart display section 722, the answer obtaining section 723, and the result display section 726 function in the same manner as the chart display section 124, the answer obtaining section 121 and the result display section 127 in the dementia test apparatus 120 shown in FIG. 3 and thus, explanation thereof is omitted.

The chart receiving section 721 receives a dementia degree test chart sent from the dementia test server 710 through the communication line 600. The answer sending section 724 sends an answer obtained by the answer obtaining section 723 to the dementia test server 710. The result receiving section 725 receives the dementia degree test result sent from the dementia test server 710. As for hardware, the communication board (see FIG. 2) of the computer system constituted as the dementia test client 720 is a main part of the above sections.

Procedure of the test of dementia degree is the same as that of the dementia test apparatus shown in FIG. 3 except that communication is established through the communication line 600, and explanation thereof is omitted.

Figure 22:
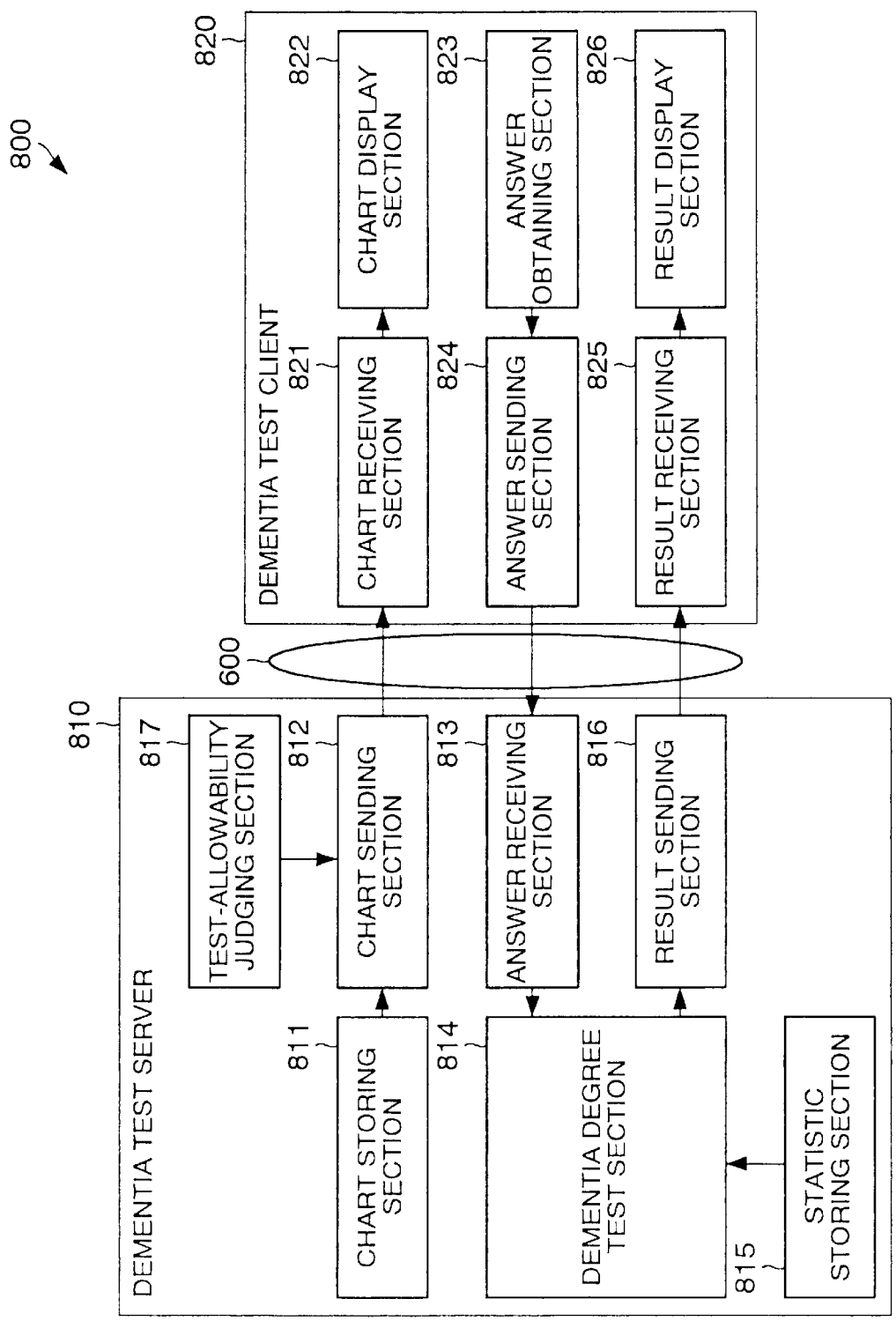
FIG. 22 is a functional block diagram of another embodiment of the dementia test system of the invention realized by the server client system shown in FIG. 20.

FIG. 22 is a functional block diagram of another embodiment of the dementia test system of the invention realized by the server client system shown in FIG. 20. Here, only one dementia test client is shown as representative.

A dementia test system 800 shown in FIG. 22 comprises a dementia test server 810 and a dementia test client 820.

A dementia test server 810 constituting a dementia test system 800 comprises a chart storing section 811, a chart sending section 812, an answer receiving section 813, a dementia degree test section 814, a statistic storing section 815, a result sending section 816, and a test-allowability judging section 817. Among them, the chart storing section 811, the dementia degree test section 814, the statistic storing section 815, and the test-allowability judging section 817 function in the same manner as the chart storing section 133, the dementia degree test section 132, the statistic storing section 135, the and the test-allowability judging section 137 constituting the dementia degree test apparatus 130 shown in FIG. 9, and explanation thereof is omitted. Like the test-allowability judging section 718 in the dementia test server 710 shown in FIG. 21, the test-allowability judging section 817 allows or prohibits a test based on the individual information sent from the dementia test client 820, and when the test was prohibited, sending of a dementia degree test chart and the dementia factor degree test chart from the chart sending section 812 is prohibited.

When the test was allowed, the chart sending section 812 reads out a dementia degree test chart and the dementia factor degree test chart from the chart storing section 811, and sends the same to the dementia test client 820. The answer receiving section 813 receives an answer to the dementia degree test chart and the dementia factor degree test chart sent from the dementia test client 820. The result sending section 816 sends the dementia degree test result or the future dementia degree transition estimation result obtained by the dementia degree test section 814 to the dementia test client 820. The communication board (see FIG. 2) of the computer system functioning mainly as the dementia test server 810 corresponds to these as hardware.

The dementia test client 820 constituting the dementia test system 800 comprises a chart receiving section 821, a chart display section 822, an answer obtaining section 823, an answer sending section 824, a result receiving section 825 and a result display section 826. Among them, the chart display section 822, the answer obtaining section 823, and the result display section 826 function in the same manner as the chart display section 134, the answer obtaining section 131 and the result display section 137 in the dementia test apparatus 130 shown in FIG. 9 and thus, explanation thereof is omitted.

The chart receiving section 821 receives the dementia degree test chart and the dementia factor degree test chart sent from the dementia test server 810 through the communication line 600. The answer sending section 824 sends an answer obtained by the answer obtaining section 823 to the dementia test server 810. The result receiving section 825 receives the dementia degree test result and the future dementia degree transition estimation result sent from the dementia test server 810. As for hardware, the communication board (see FIG. 2) of the computer system operating as the dementia test client 820 is a main part of the above sections.

Procedure of the test of dementia degree is the same as that of the dementia test apparatus 130 shown in FIG. 9 except that communication is established through the communication line 600, and explanation thereof is omitted.

Figure 23:
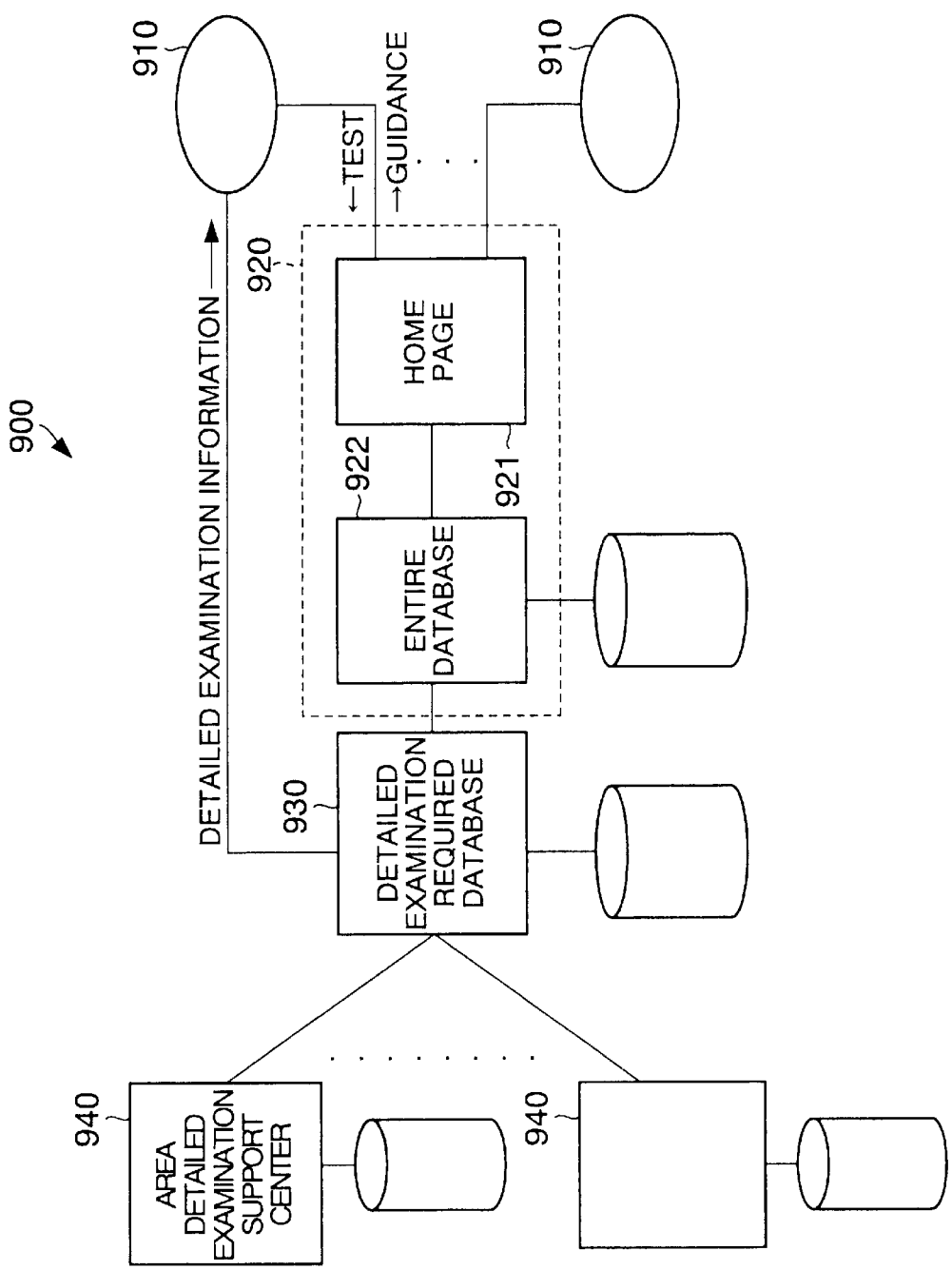
FIG. 23 shows the entire image of early-dementia finding and preventing system including the dementia test system of the invention.

FIG. 23 shows the entire image of early-dementia finding and preventing system including an embodiment of the dementia test system of the invention.

As shown in FIG. 23, the early-dementia finding and preventing system 900 comprises a personal computer 910 of a testee, a web server 920 comprising a home page 921 and entire database 922, a detailed examination required database 930 and a detailed examination support system 940 of each region.

The personal computer 910 of the testee is a terminal used by a person taking a test. Other than the family personal computer, a portable terminal may be utilized if the terminal can be connected to the Internet.

The home page 921 is constructed in the web server 920. The home page 921 collects basic data, test result and the like of a testee, executes a test, display device which was fed back from the database, and functions as a window connecting the database and a client.

The entire database 922 stores and manages the data of all testees, and performs statistical analysis of the data.

The detailed examination required database 930 is a server which receives data of a testee who was judged that a detailed examination was necessary from the entire database 922, for example, a testee having a test result lower than H1 "initial dementia" described in FIG. 19, sends a notice of precise test to that testee, and sends information to an area detailed examination support center. The detailed examination required database 930 serves such that nationwide detailed examination support centers and medical institutions can access the detailed examination required database 930 using common format, and they can be supported from anywhere.

In the area detailed examination support center 940, service such as a detailed examination and rehabilitation is given by a doctor or district nurse to a person who was judged that a detailed examination is necessary.

A series of stream of the system is as follows. First, a testee inputs basic data on the home page and receives a test. A result of the test is processed by the entire database 922, and the test result is fed back to the testee. The data at that time is stored and managed in the entire database 922. Here, if the entire database 922 judges that a detailed examination is necessary, the data is sent to the detailed examination required database 930, and contact is made with the detailed examination support center 940 and the testee. Then, the detailed examination and rehabilitation if necessary are recommended.

As described above, according to the present invention, the dementia can be tested in early stage and easily.

What is claimed is:

1. A dementia test apparatus comprising:
   an answer obtaining section for obtaining an answer of a testee to a dementia degree test chart which requires a plurality kinds of judgements at the same time and obtains an answer in such a form that correction of judgement is objectively judged; and
   a dementia degree test section for testing a dementia degree indicative of a degree of dementia of the testee based on the answer obtained by the answer obtaining section.

2. A dementia test apparatus according to claim 1, further comprising a chart storing section for storing the dementia degree test chart, and a chart display section for displaying the dementia degree test chart.

3. A dementia test apparatus in which when a plurality of testees are divided into a plurality of groups based on a predetermined criterion, comprising a statistic storing section for storing a statistic processing result of answer of the testees in each of the groups, wherein
   the dementia degree test section tests a position in the statistic processing result of the answer to the dementia degree test chart of a current testee obtained by on answer obtaining section.

4. A dementia test apparatus according to claim 1, further comprising a dementia degree storing section for storing a relationship between the answer to the dementia degree test chart and a dementia degree, wherein
   the dementia degree test section refers to the dementia degree storing section, and tests a dementia degree of the current testee from the answer to the dementia degree test chart of the current testee obtained by the answer obtaining section.

5. A dementia test apparatus according to claim 1, further comprising a result display section for displaying a dementia degree test result obtained by the dementia degree test section.

6. A dementia test apparatus according to claim 1, further comprising a test-allowability judging section for allowing or prohibiting a test-requiring person depending whether a predetermined time has been elapsed after the test-requiring person received the test last time.

7. A dementia test apparatus comprising:
   an answer obtaining section for obtaining an answer of a testee to both a dementia degree test chart which requires a plurality kinds of judgement at the same time and obtains an answer in such a form that correction of the judgement is objectively judged, and a dementia factor degree test chart comprising a combination of a plurality of question concerning sensibility and a plurality of answers alternatively selected from questions prepared for each of the former questions; and
   a dementia degree test section for testing a dementia degree indicative of a current dementia degree of the testee, and for estimating transition of future dementia degree of the testee based on an answer obtained by the answer obtaining section.

8. A dementia test apparatus according to claim 7, further comprising a chart storing section for storing the dementia degree test chart and a dementia factor degree test chart, and a chart display section for displaying the dementia degree test chart and the dementia factor degree test chart.

9. A dementia test apparatus according to claim 7, further comprising a statistic storing section for storing a statistic processing result of answers of the testees to both the dementia degree test chart and the dementia factor degree test chart in each group when a plurality of testees are divided into a plurality of groups based on a predetermined criterion, wherein
   the dementia degree test section tests a current position of the statistic processing result and estimates a variation of a future position of the answer of the current testee obtained by the answer obtaining section.

10. A dementia test apparatus according to claim 7, further comprising a result display section for displaying a dementia degree test result obtained by the dementia degree test section and a transition estimation result of the future dementia degree.

11. A dementia test apparatus according to claim 7, further comprising a test-allowability judging section for allowing or prohibiting a test-requiring person depending whether a predetermined time has been elapsed after the test-requiring person received the test last time.

12. A dementia test server in a dementia test system comprising a dementia test server and a dementia test client connected to each other through a communication line, comprising:
   a chart storing section for storing a dementia degree test chart which requires a plurality kinds of judgement at the same time and obtains an answer in such a form that correction of judgement is objectively judged;
   a chart sending section for sending the dementia degree test chart to the dementia test client;
   an answer receiving section for receiving an answer to the dementia degree test chart from the dementia test client; and
   a dementia degree test section for testing a dementia degree indicative of a degree of dementia of the testee based on the answer obtained by the answer obtaining section.

13. A dementia test server according to claim 12, further comprising a statistic storing section for storing a statistic processing result of answers to the dementia degree test chart in each group when a plurality of testees are divided into a plurality of groups based on a predetermined criterion, wherein the dementia degree test section tests a position of the statistic processing result of an answer of a current testee received by the answer receiving section.

14. A dementia test server according to claim 12, further comprising a dementia degree storing section for storing a relationship between a dementia degree and an answer to the dementia degree test chart, wherein the dementia degree test section refers to the dementia degree storing section, and tests a dementia degree of the current testee from the answer of the current testee received by the answer receiving section.

15. A dementia test server according to claim 12, further comprising a result sending section for sending a dementia degree test result obtained by the dementia degree test section to the dementia test client.

16. A dementia test server according to claim 12, further comprising a test-allowability judging section for allowing or prohibiting a test-requiring person depending whether a predetermined time has been elapsed after the test-requiring person received the test last time.

17. A dementia test client in a dementia test system comprising a dementia test server and a dementia test client connected to each other through a communication line, comprising:

a chart receiving section for receiving a dementia degree test chart which requires a plurality kind of judgement at the same time and obtains an answer in such a form that correction of judgement is objectively judged sent from the dementia test server;

a chart display section for displaying a dementia degree test chart received by the chart receiving section;

an answer obtaining section for obtaining an answer to a dementia degree test chart displayed on the chart display section according to operation; and an answer sending section for sending an answer obtained by the answer obtaining section to the dementia test server.

18. A dementia test client according to claim 17, further comprising: a result receiving section for receiving a dementia degree test result obtained at and sent from the dementia test server by sending the answer to the dementia test server; and a result display section for displaying a dementia degree test result received by the result receiving section.

19. A dementia test server in a dementia test server comprising a dementia test server and a dementia test client connected to each other through a communication line, comprising:

a chart storing section for storing both a dementia degree test chart which requires a plurality kinds of judgement at the same time and obtains an answer in such a form that correction of the judgement is objectively judged, and a dementia factor degree test chart comprising a combination of a plurality of question concerning sensibility and a plurality of answers alternatively selected from questions prepared for each of the former questions;

a chart sending section for sending both the dementia degree test chart and the dementia factor degree test chart to the dementia test client;

an answer receiving section for receiving an answer to the dementia degree test chart and the dementia factor degree test chart from the dementia test client; and a dementia degree test section for testing a dementia degree indicative of a current degree of dementia of a testee and for estimating a transition of a future dementia degree of the testee based on the answer received by the answer receiving section.

20. A dementia test server according to claim 19, further comprising a statistic storing section for storing a statistic processing result of answers of the testees to both the dementia degree test chart and the dementia factor degree test chart in each group when a plurality of testees are divided into a plurality of groups based on a predetermined criterion, wherein the dementia degree test section tests a current position of the statistic processing result of the answer of the current testee received by the answer receiving section, and estimates a variation of a future position.

21. A dementia test server according to claim 19, further comprising a result sending section for sending a dementia degree test result obtained by the dementia degree test section and a transition estimation result of the future dementia degree to the dementia test client.

22. A dementia test server according to claim 19, further comprising a test-allowability judging section for allowing or prohibiting a test-requiring person depending whether a predetermined time has been elapsed after the test-requiring person received the test last time.

23. A dementia test client in a dementia test server comprising a dementia test server and a dementia test client connected to each other through a communication line, comprising:

a chart receiving section for receiving both a dementia degree test which requires a plurality kinds of judgement at the same time and obtains an answer in such a form that correction of the judgement is objectively judged, and a dementia factor degree test chart comprising a combination of a plurality of question concerning sensibility and a plurality of answers alternatively selected from questions prepared for each of the former questions;

a chart display section for displaying a dementia degree test chart and a dementia factor degree test chart received by the chart receiving section;

an answer obtaining section for obtaining answers to the dementia degree test chart and the dementia factor degree test chart displayed on the chart display section according to operation; and an answer sending section for sending an answer obtained by the answer obtaining section to the dementia test server.

24. A dementia test client according to claim 23, further comprising a result receiving section for receiving a dementia degree test result and a transition estimation result of a future dementia degree obtained from the dementia test server by sending the answer sent from the dementia test server to the dementia test server, and a result display section for displaying a dementia degree test result and a transition estimation result of a future dementia degree received by the result receiving section.

25. A dementia test system comprising a dementia test server and a dementia test client connected to each other through a communication line, wherein the dementia test server comprises:
- a chart storing section for storing a dementia degree test chart which requires plurality kinds of judgements at the same time and obtains an answer in such a form that correction of judgement is objectively judged;
- a chart sending section for sending the dementia degree test chart to the dementia test client;
- an answer receiving section for receiving an answer to the dementia degree test chart from the dementia test client; and
- a dementia degree test section for testing a dementia degree of the testee based on an answer obtained by the answer receiving section, and wherein
  the dementia test client comprises:
  - chart receiving section for receiving the dementia degree test chart sent from the dementia test server;
  - a chart display section for displaying the dementia degree test chart received by the chart receiving section;
  - an answer obtaining section for obtaining an answer sending section to the dementia degree test chart displayed on the chart display section according to operation; and
  - an answer sending section for sending the answer obtained by the answer obtaining section to the dementia test server.

26. A dementia test system comprising a dementia test server and a dementia test client connected to each other through a communication line, wherein
the dementia test server comprises:
- a chart storing section for storing both a dementia degree test chart which requires a plurality kinds of judgements at the same time and obtains an answer in such a form that correction of judgement is objectively judged, and a dementia factor degree test chart comprising a combination of a plurality of question concerning sensibility and a plurality of answers alternatively selected from questions prepared for each of the former questions;
- a chart sending section for sending both the dementia degree test chart and the dementia factor degree test chart to the dementia test client;
- an answer receiving section for receiving an answer to the dementia degree test chart and the dementia factor degree test chart from the dementia test client; and
- a dementia degree test section for testing a dementia degree indicative of a current degree of dementia of a testee and for estimating a transition of a future dementia degree based on the answer received by the answer receiving section, and wherein
  the dementia test client comprises:
  - a chart receiving section for receiving both a dementia degree test which requires plurality kinds of judgements at the same time and obtains an answer in such a form that correction of judgement is objectively judged, and a dementia factor degree test chart comprising a combination of a plurality of question concerning sensibility and a plurality of answers alternatively selected from questions prepared for each of the former questions;
  - a chart display section for displaying a dementia degree test chart and a dementia factor degree test chart received by the chart receiving section;
  - an answer obtaining section for obtaining answers to the dementia degree test chart and the dementia factor degree test chart displayed on the chart display section according to operation; and
  - an answer sending section for sending an answer obtained by the answer obtaining section to the dementia test server.

* * * * *